United States Patent
King-Smith et al.

(10) Patent No.: US 9,869,657 B2
(45) Date of Patent: Jan. 16, 2018

(54) ION SENSITIVE DEVICE AND METHOD OF FABRICATION

(71) Applicant: ELEMENTAL SENSOR LLC, Aptos, CA (US)

(72) Inventors: Oliver King-Smith, Aptos, CA (US); Eric Kerstan Hoobler, Santa Crus, CA (US)

(73) Assignee: Elemental Sensor LLC, Aptos, CA (US)

( * ) Notice: Subject to any disclaimer, the term of this patent is extended or adjusted under 35 U.S.C. 154(b) by 71 days.

(21) Appl. No.: 14/257,935

(22) Filed: Apr. 21, 2014

(65) Prior Publication Data

US 2014/0348707 A1   Nov. 27, 2014

Related U.S. Application Data

(60) Provisional application No. 61/814,300, filed on Apr. 21, 2013.

(51) Int. Cl.
    *H01L 29/812*     (2006.01)
    *G01N 27/414*     (2006.01)
    *H01L 21/02*     (2006.01)

(52) U.S. Cl.
    CPC ... *G01N 27/4148* (2013.01); *H01L 21/02172* (2013.01); *H01L 21/02178* (2013.01); *H01L 21/02183* (2013.01); *H01L 21/02186* (2013.01); *H01L 21/02192* (2013.01); *H01L 21/02318* (2013.01)

(58) Field of Classification Search
    CPC .......... G01N 27/4148; H01L 21/02172; H01L 21/02178; H01L 21/02183; H01L 21/02186; H01L 21/02192; H01L 21/02318
    See application file for complete search history.

(56) References Cited

U.S. PATENT DOCUMENTS 5,825,063 A    10/1998   Diorio et al.
2010/0137143 A1*   6/2010   Rothberg ............. C12Q 1/6874
                                                         506/2

OTHER PUBLICATIONS

Zayats, Maya, et a. "Imprinting of specific molecular recognition sites in inorganic and organic thin layer membranes associated with ion-sensitive field effect transistors." Tetrahedon 58.4 (2002): 815-824.*
Park, Jong Kyung, et al. "Graphene gate electrode for MOS structure-based electronic devices." Nano letters 11.12 (2011): 5383-5386.*
Morgenshtein, Sudakov-Boreysha, Dinnar, Jakobson, and Nemirovsky. "CMOS readout circuitry for ISFET microsystems." Sensors and Actuators B 97 (2004) 122-131.

(Continued)

*Primary Examiner* — Robert Eom
(74) *Attorney, Agent, or Firm* — Karen Canaan; CanaanLaw, P.C.

(57) ABSTRACT

A sol-gel deposition technique that forms ion sensitive layers is compatible with CMOS fabrication methods and is applied to build sensors of concentrations of solutions of selected target ions. The ion sensitive sensor may be formed on an exposed portion of a signal trace of a printed circuit board. Additionally, the ion sensitive layer may be formed within an ion sensitive field effect transistor.

35 Claims, 16 Drawing Sheets

(56) References Cited

OTHER PUBLICATIONS

Hammond, P.A. and Ali, D. and Cumming, D.R.S. (2004) Design of a single-chip pH sensor using a conventional 0.6-• m CMOS process. IEEE Sensors Journal 4(6):pp. 706-712. Jan. 8.
Sheng-Ren Chang and Hsin Chen.Sensors 9, 8336-8348 "A CMOS-Compatible, Low-Noise ISF E T Based on High Efficiency Ion-Modulated Lateral-Bipolar Conduction." Oct. 2009.
Palan et al., CMOS ISFET-Based Structures for Biomedical Applications, 1st Annual International IEEE-EMBS Special Topic Conference on Microtechnologies in Medicine and Biology—Proceedings. Piscataway: IEEE, pp. 502-506 (2000) (ISBN 0/7803-6603-4).
Camenzind, Designing Analog Chips, Feb. 2005, published at www.designinganalogchips.com.
Ren, Development of Aluminum Oxide (Al2O3) Gate Dielectric Protein Biosensor under Physiologic Buffer, Graduate Thesis (in Electrical and Computer Engineering) of Fang Ren, The Ohio State University, 2012.

* cited by examiner

ION SENSITIVE DEVICE AND METHOD OF FABRICATION

CO-PENDING US PROVISIONAL PATENT APPLICATION

The present Nonprovisional Patent Application is a Continuation-in-Part Patent Application of U.S. Provisional Patent Application Ser. No. 61/814,300, filed on Apr. 21, 2013 and titled "Chemically Sensitive ISFET". The present Nonprovisional Patent Application claims the priority date of Provisional Patent Application Ser. No. 61/814,300. Furthermore, Provisional Patent Application Ser. No. 61/814,300 is hereby incorporated into the present Nonprovisional Patent Application in its entirety and for all purposes.

BACKGROUND OF THE INVENTION

Field of the Invention

The present invention relates to ion sensitive electronic devices and the manufacture thereat and in particular a manufacturing method compatible with CMOS fabrication processes and ion sensitive devices produced by a method compatible with CMOS fabrication processes.

Description of the Related Art

There is a long felt need for durable electronic sensors that can reliably and accurately measure a concentration of a selected ion or molecule within a solution, such as a concentration of Malic acid or Lactic acid within a fermenting solution of wine. Yet the prior art fails to optimally provide sensors and methods of manufacturing that are compatible complementary metal-oxide semiconductor fabrication techniques.

The prior art does provide ion sensitive field effect transistors (hereinafter, "ISFETs") and Chemically Sensitive Field Effect Transistors (or, "ChemFETs") that are intended to reliably and durably generate measurable electrical behaviors that indicate a concentration of a specific target ion or target molecule within a liquid solution. The scope of meaning of the term ISFET as used within the present disclosure includes a Field Effect Transistor that exhibits chemically sensitive electrical qualities, parameters and/or behavior.

In 1970, Bergveld invented a semiconductor device that was chemically sensitive. Much work has been done to commercialize these technologies. A number of companies already sell ISFET sensors such as: D+T Microelectronica, and Sentron Europe By. In addition other companies sell complete ISFET meters such as Hach and Honeywell's DURAFET™. These commercial ISFETs work well, but they are made in non-standard ways. They often use special-purpose materials, such as Tantalum Oxide. In addition when forming the sensing surfaces they have to use a high temperature process which prevents the use of metal layers, which would melt and delaminate the chip. These high temperature prior art techniques generally subject circuit elements to temperatures above 300 degrees Celsius and thereby present challenges in cost-effectively producing sensing surfaces that are specifically sensitive to any molecule or ion other than hydronium. In particular, these prior art high temperature techniques present technical and economic challenges in commercially producing ISFETs that are sensitized to any ion or molecule other than hydronium. Both of these requirements mean that the prior art ISFETs need to be manufactured in a custom fabrication plant. This requirement makes prior art ISFETs expensive to produce, which in turn limits their application.

The prior art further includes applying sol-gel materials and techniques to deposit an ion-specific sensitizing film on a top layer of a gate oxide of a metal-oxide semiconductor field effect transistor. The prior art sensitizing film is preferably selected to be particularly electrically sensitive to a target molecule such that the influence of the gate on the source/drain current of the instant field effect transistor will reliably indicate a concentration of the target molecule within a solution to which the instant field effect transistor is exposed.

The literature of depositing establishing an ion-specific sensitizing film on a metal oxide, wherein the metal oxide is electrically coupled with a gate of a field effect transistor, often refers to the active ingredient of the sensitizing film as an ionophore. It is understood that the term "ionophore" is widely but loosely used in the art to indicate a category of possible seed molecules that create channels in a comprising polymer film and thereby increase an ion-specific sensitivity of the combination of the polymer film and the coupled metal oxide. The origin of the term ionophore limited the scope of the meaning of this term to a lipid-soluble molecule usually synthesized by microorganisms to transport ions across the lipid bilayer of the cell membrane. The use of this term ionophore is thus avoided in the present disclosure and the term "film seed molecule" is meant to designate a molecule or ion that is suitable for positioning within a film or thin layer and upon a top surface of a metal oxide sensing material and that affects the behavior of a gate of a field effect transistor.

In another aspect of the background of the present invention, the sol-gel process is a wet-chemical technique widely used in the fields of materials science and ceramic engineering. Such methods are used primarily for the deposition of materials, including but not limited to metal oxides. Starting from a colloidal solution (or the "sol" state) that acts as the precursor for an integrated network (or the "gel" state) of either discrete particles or network polymers. Typical components of sol-gel mixtures include, but are not limited to, metal alkoxides and metal salts, including but not limited to chlorides, nitrides and acetates, which undergo various forms of hydrolysis and polycondensation reactions in transitioning from sol state into a gel state.

The prior art further provides applications of imprinting molecular polymers wherein selected seed molecules are introduced into a sol-gel mixture prior to placement of the sol-gel mixture as an element of an electronic circuit. A molecularly imprinted polymer (hereinafter, "MIP") is a polymer that has been processed using the molecular imprinting technique which leaves cavities in polymer matrix with affinity to a chosen "template" molecule. The process usually involves initiating the polymerization of monomers in the presence of a template seed molecule that is extracted afterwards, thus leaving complementary cavities behind. These polymers have affinity for the original molecule and have been used in applications such as chemical separations, catalysis, and molecular sensors.

The term "sol-gel seed molecule" is used within the present disclosure to distinguish molecules introduced into a metal oxide or sol-gel to form a MIP from those materials identified as film seed molecules.

An obvious way to make ISFETs less expensive is to try and make them in a conventional semiconductor fabrication plant. The prior art does include applications of standard CMOS processes to make ISFETs. The early CMOS ISFETS were developed in the 1980s but were not widely accepted commercial applications. Prior art CMOS ISFETs suffer from drift and hysteresis, which makes them difficult to commercialize. Drift causes the output voltage of the ISFET to change over time even in a constant environment. Hysteresis causes the output voltage to not return to the same level when the chemical concentration changes from A to B and then back to A. The hysteresis change in voltage is different than what would be expected by just the drift if the ISFET had been held at concentration A. Both drift and hysteresis are severe in conventional CMOS ISFETs.

Some commercial applications for prior art CMOS ISFETs have been found. Some companies have managed to use CMOS ISFET sensors in high throughput DNA screening. However, prior art CMOS ISFETs of this type primarily detect the binary presence of a genetic DNA base pair, as opposed to the concentration.

While the prior art discloses sol-gel deposition technology to be applicable to ISFET fabrication, the prior art fails to provide (a.) optimal sol-gel deposition techniques that form effective ion sensitive layers at temperatures below 100 degrees Celsius on electrically conductive traces, (b.) sol-gel processes compatible with complementary metal-oxide semiconductor (hereinafter, "CMOS") fabrication methods, or (c.) CMOS devices having ion detecting films created by sol-gel methods.

It will be appreciated from the foregoing that there is a long-felt need for a transistor based chemical sensor that is less expensive than a conventional ISFET but that has higher performance characteristics than prior art CMOS ISFETs as manufactured in a conventional fabrication operation. Particularly desired would be a low-cost chemically sensitive sensor that (a.) may be more cost-effectively formed on a printed circuit board; or (b.) may be produced by commonly CMOS fabrication facilities, does not show unacceptable hysteresis and is capable of measuring the concentration of target molecules in either simple solutions or complex mixtures.

SUMMARY OF THE INVENTION

Toward this object and other objects that are made obvious to one of ordinary skill in the art in light of the present disclosure, an ion sensitive device that is adapted to present electrically detectable behavior that is especially sensitive to exposure to the presence of a target ion in solution and method of manufacture of said invented ion sensitive device is provided. In one aspect of the method of the present invention (hereinafter, "the invented method") a sol-gel mixture is applied as a component of an ion sensitive sensor, such as a CMOS ISFET or a substrate with an electrically conductive trace. It is understood that a detection of a concentration of a target ion in a liquid solution is the most common modality of the invented method.

The scope of the invented method as disclosed herein is also applicable to BiCMOS semiconductor fabrication process and BiPolar semiconductor fabrication processes.

In an optional aspect of the invented method, the sol-gel mixture may be molecularly imprinted with either a target ion or another sol-gel seeding molecule that causes the resultant sol-gel mixture in its gel state to be particularly electrically sensitive to the target ion.

In another optional aspect of the invented method, an ion sensitive polymer layer comprising film seed molecules may be positioned or deposited on an external surface of a sol-gel mixture, wherein the sol-gel mixture is positioned electrically coupled to either a field effect transistor or an electrically conductive structure.

In yet another optional aspect of the invented method, an electrically conductive barrier material is disposed between the sol-gel mixture and (a.) an electrically conductive component of a field effect transistor that affects the behavior of the instant field effect transistor or (b.) a pad or length of an electrically conductive trace or element of a printed circuit board or other suitable support structure known in the art.

In a still additional optional aspect of the invented method, two invented sensors may be placed on a same support printed circuit or other insulating substrate, within a same semiconductor die, wherein (a.) a metal oxide of a first sol-gel solution of a first sensor has been molecularly imprinted with sol-gel seeding molecules and/or an ion sensitive polymer layer has been positioned on a top surface of the first sol-gel mixture, and (b.) a second sol-gel mixture of the second sensor contains that same metal oxide as the first sol-gel mixture but has neither been templated with sol-gel seeding nor enhanced by a positioning of an ion sensitive polymer layer. The relative electrical behavior of these two sensors may be simultaneously or contemporaneously observed in order to increase an accuracy of measurement of a concentration of a target molecule in a solution with which both sensors are in contact. The state and performance of a reference electrode or a quasi or pseudo reference electrode may also be accessed and applied in relation to the electrical performance of these two sensors in order to further increase an accuracy of measurement of an instantaneous concentration of the target molecule in the solution.

According to another additional aspect of the method of the present invention, au ISFET and a method of fabricating ISFETs with sol-gel materials that is compatible with CMOS fabrication techniques is provided.

In an alternative optional aspect of the invented method applicable to CMOS ISFET fabrication, the sol-gel is coupled with au electrically conductive structure that affects the performance of a gate of a field effect transistor that is formed within a semiconductor die.

In another optional aspect of the invented method, a field effect transistor may be manufactured with a sol-gel process that is compatible with CMOS fabrication technology. The optional barrier material may be graphene or another suitable material known in the art that is resistive to contamination or permitted passage of material from the top layer to the ion sensitive material. It is preferred that the barrier material presented no more than approximately a megaohm of electrical current resistance between the sol-gel and another circuit element, such as a gate of a field effect transistor or a trace of printed circuit board.

The ion sensitive material may be or, in singularity or combination, a metal oxide that includes Titanium, Tantalum, Vanadium, Aluminum, Silicon, Yttrium, Tin, one or more alloys of Lead and Titanium, Silicon Nitride, and/or other metals and alloys of suitable materials known in the art.

In a still other optional aspect of the invented method, the sensitivity of the ion sensitive material of the sol-gel to a particular target ion may be increased by an application of molecular imprinting, wherein a seed material is introduced in a sol-gel prior to inclusion of the sol-gel as a component of an ISFET or other ion sensitive sensor. The seed material may be or include the target ion and/or a molecule different from the target ion that may be introduced to the sol-gel to allow greater selectivity and or sensitivity of an electrochemical sensor to a particular chemical species. The sol-gel seed material may optionally be partially, entirely, substantively or selectively removed from the sal-gel mixture in various alternate preferred embodiments of the invented method. As indicated previously within the present disclosure, the term "sol-gel seed" is used within the present disclosure to distinguish molecules introduced into a sol-gel material in a molecular imprinting process from those materials identified as film seed molecules. In a yet another optional aspect of the invented method, a first CMOS ISFET comprising a given ion sensitive material may be coupled with a second CMOS ISFET comprising the same ion sensitive material that has been treated with a molecular imprinting process to increase or foreseeably alter the ion-specific sensitivity of the second CMOS ISFET to a same target ion. Alternatively and optionally, a polymer film comprising of film seed molecules may have been positioned at a top surface of the ion sensitive material of the second CMOS ISFET to increase or foreseeably alter the ion-specific sensitivity of the second CMOS ISFET to the same target ion.

Additionally and optionally, a reference electrode may be electrically coupled with the first CMOS ISFET and or the second CMOS ISFET and applied by a measurement circuit to more accurately generate concentration measurement of the target ion with a solution. Alternatively and optionally, a pseudo reference electrode may be electrically coupled with the first CMOS ISFET and or the second CMOS ISFET and applied by a measurement circuit to more accurately generate concentration measurement of the target ion with a solution.

The present invention can bring chemical analysis to consumer, agricultural, medical, and industrial markets. In another embodiment several invented sensors of alternate construction can be used to separately detect each of several target chemicals simultaneously. In one embodiment of the invented method a combination of sensors can be used to monitor wine fermentation and aging inside oak barrels. In another embodiment of the invented method a combination of invented sensors are used to monitor water quality in creeks and watersheds. In another embodiment of the invented method a combination of invented sensors are used to monitor and recommend appropriate adjustments in residential pools and hot tubs. In another embodiment of the invented method one or more invented sensors are used for urinalysis to assist performance athletes in their training and dietary habits. In another embodiment of the invented method a combination of invented sensors are used to assist people who are dieting. In another embodiment of the invented method one or more invented sensors are used to monitor aquariums. In another embodiment of the invented method a combination of invented sensors are used to assist people who are being treated by alternative medicine. In another embodiment of the invented method, the sensors are used in fuel cells and batteries to measure SOC and health of the devices. In another embodiment of the invented method, the sensors are used to speed up and improve dialysis. In another embodiment of the invented method, the sensors are used to measure homocysteine in sweat, to monitor patients' risk factors to endothelial injury and other diseases. In another embodiment of the invented method a combination of invented sensors are used in medical devices.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

INCORPORATION BY REFERENCE

All publications mentioned herein are incorporated herein by reference to 15 disclose and describe the methods and/or materials in connection with which the publications are cited. All publications, patents, and patent applications mentioned in this specification are herein incorporated by reference in their entirety and for all purposes to the same extent as if each individual publication, patent, or patent application was specifically and individually indicated to be incorporated by reference.

Such incorporations include U.S. Pat. No. 6,905,896 B2 titled "SnO2 ISFET device, manufacturing method, and methods and apparatus for use thereof"; U.S. Pat. No. 7,190,013 titled "SnO2 ISFET device, manufacturing method, and methods and apparatus for use thereof"; U.S. Pat. No. 7,067,343 titled "ISFETs fabrication method" and Patent Application Publication No. WO2009151309 of PCT Patent Application Publication PCT/MY2008/000172 titled "Method and system for applying ion-selective membrane on isfet surface".

The publications discussed or mentioned herein are provided solely for their disclosure prior to the filing date of the present application. Nothing herein is to be construed as an admission that the present invention is not entitled to antedate such publication by virtue of prior invention. Furthermore, the dates of publication provided herein may differ from the actual publication dates which may need to be independently confirmed.

BRIEF DESCRIPTION OF THE FIGURES

These, and further features of the invention, may be better understood with reference to the accompanying specification and drawings depicting the preferred embodiment, in which.

The Figures depict various embodiments of the present invention for purposes of illustration only. One skilled in the art will readily recognize from the following discussion that alternative embodiments of the structures and methods illustrated herein may be employed without departing from the principles of the invention described herein.

DETAILED DESCRIPTION

It is to be understood that this invention is not limited to particular aspects of the present invention described, as such may, of course, vary. It is also to be understood that the terminology used herein is for the purpose of describing particular aspects only, and is not intended to be limiting, since the scope of the present invention will be limited only by the appended claims.

Figure 1:
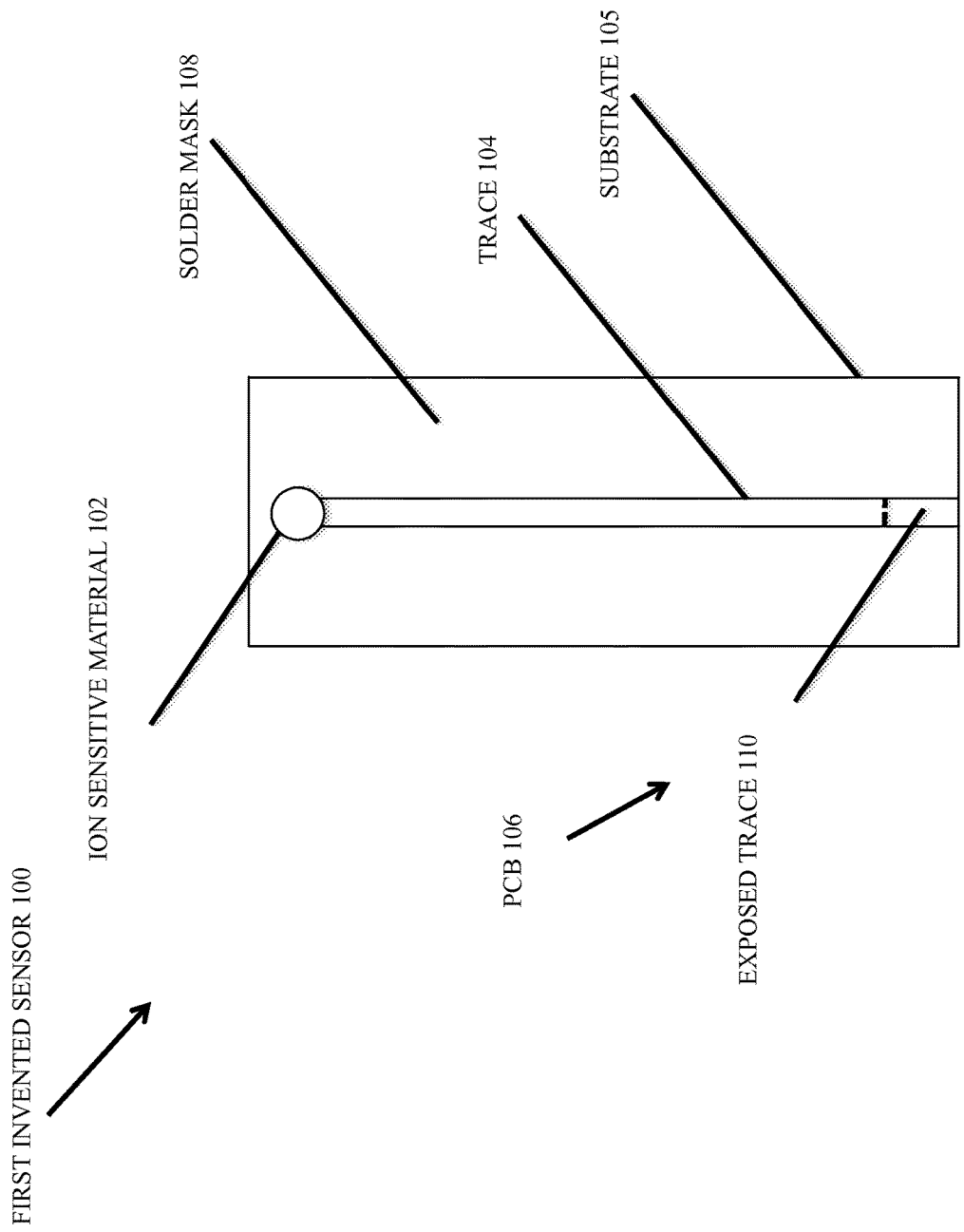
FIG. 1 is a top view of a first embodiment of the present invention that shows an invented sensor comprising an ion sensitive material electrically coupled with a trace of a printed circuit board.

Referring generally to the Figures and particularly to FIG. 1, FIG. 1 is a top view of an invented sensor 100 that includes an ion sensitive material 102 electrically coupled with an electrically conductive trace 104 of a printed circuit board 106 (hereinafter "PCB" 106). The trace 104 may comprise copper and is affixed to an insulating nonconductive substrate 105 of the PCB 106. The trace 104 extends from the ion sensitive material 102. A solder mask 108 in combination with the insulating nonconductive substrate 105 substantively shields the trace 104 from physical damage. An exposed trace length 110 of the trace 104 is not covered by the solder mask 108 and thereby allows electrical coupling of the first invented sensor 100 to measurement equipment.

Figure 2:
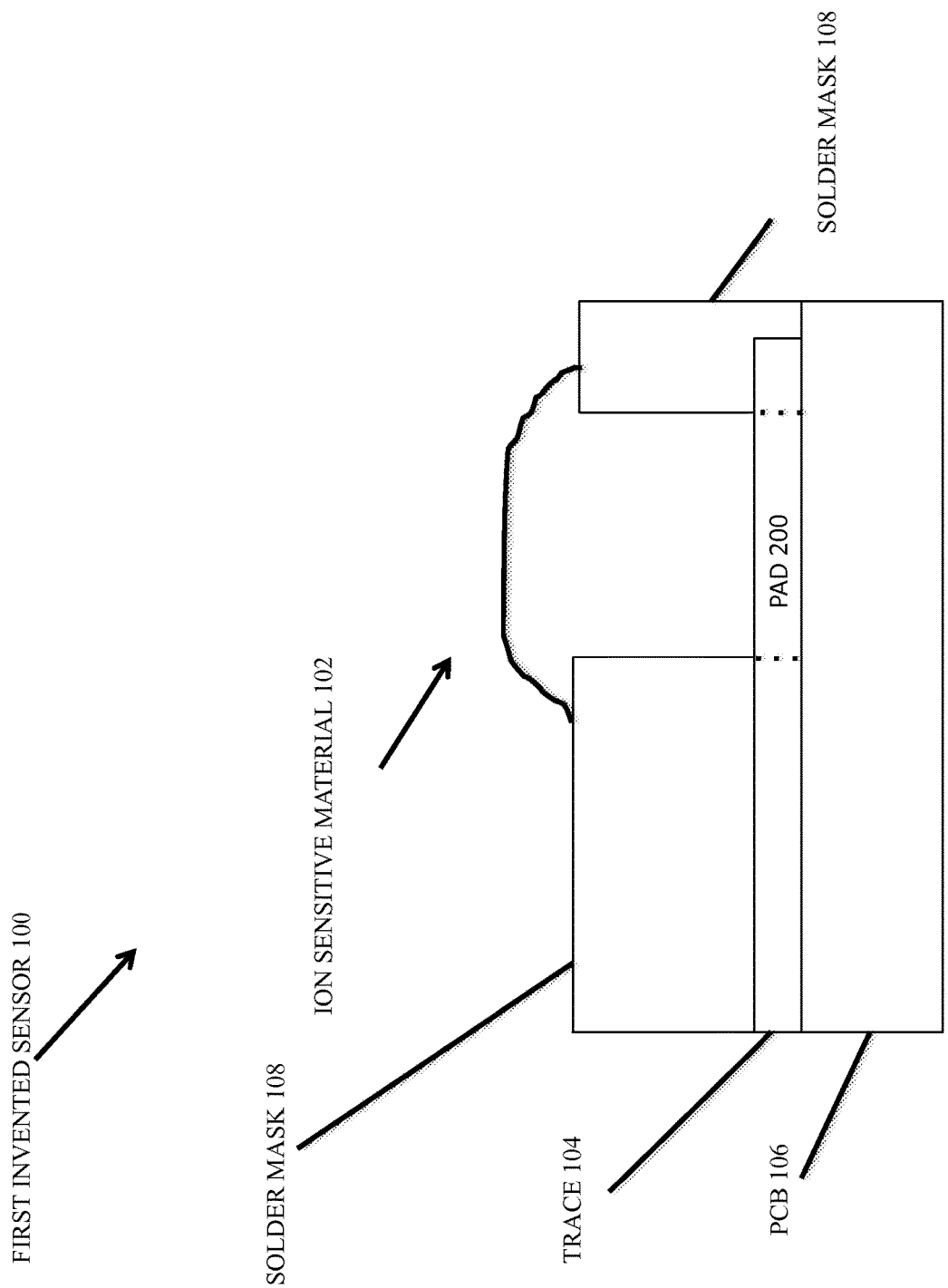
FIG. 2 is a detailed cut away side view of the invented sensor of the first version of FIG. 1 and illustrating the composition of the invented sensor.

Referring generally to the Figures and particularly to FIG. 2, FIG. 2 is a detailed cut away side view of the first invented sensor 100. The solder mask 108 has been relieved to expose a pad 200 of the trace 104. The ion sensitive material 102, preferably comprising a metal oxide deposited in a sol-gel process that preferably did not exceed 200 degrees Celsius and more preferably did not exceed 100 degrees Celsius.

The ion sensitive material 102 is selected to be particularly and measurably sensitive to concentration of one or more target ions. It is known in the art that metal oxides by themselves are generally sensitive to hydronium and are therefore generally appropriate to compose the ion sensitive material 102 in a pH sensor, Of course, exceptions exist, wherein Copper Oxide bonds with Hydrogen Sulfide and is therefore appropriate as the ion sensitive material 102 of a sensor of Hydrogen Sulfide.

For example, forming the ion sensitive material 102 with Titanium Dioxide (TiO2) by a sol-gel process is useful in measuring pH in solutions having a water solvent. Regarding pH measurements of solutions, ISFETs having oxides comprising Tantalum tend to be more accurate in measuring pH, but Tantalum and Tantalum oxides are toxic, whereas Titanium Oxides are believed in the art to be fairly benign. Furthermore, in an alternate embodiment of the invented method wherein the first invented sensor 100 comprises an ion sensitive material 102 that is or comprises Titanium Dioxide, the ion sensitive material 102 by itself, and without additional molecular imprinting or the addition of the film polymer 404, the ion sensitive material is sensitive to, and may be applied to measure, concentrations of both Malic acid and Lactic acid.

Figure 3:
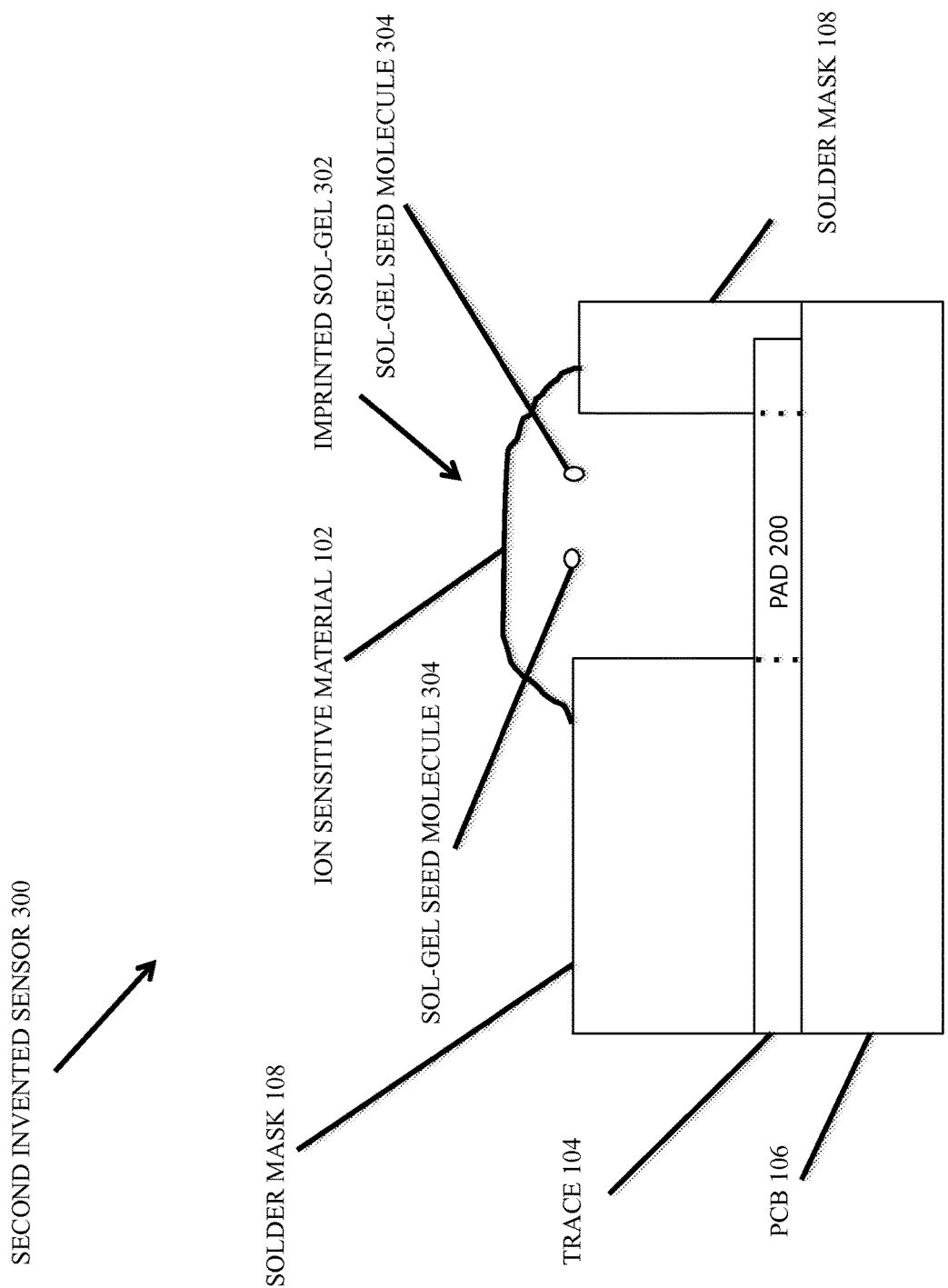
FIG. 3 is a detailed cut away side view of the invented sensor of the first version of FIG. 1 and illustrating the composition of the invented sensor after a process of molecularly imprinting the ion sensitive material with a plurality of sol-gel molecules.

Referring generally to the Figures and particularly to FIG. 3, FIG. 3 is a detailed cut away side view of a second invented sensor 300 that further comprises a molecularly imprinted sol-gel matrix 302. A plurality of sol-gel seed molecules 304 that were introduced into the ion sensitive material 102 to form the imprinted sol-gel matrix 302.

In one example of a sol-gel process, the metal oxide TiO2 forms a polymer to create the imprinted sol-gel matrix 302, and the resulting polymer may be imprinted with either the target ions of Malic acid or an alternate sol-gel seed molecule 304, such as Phenylalanine or b-Phenyllactic acid. This formation of a molecular imprinted polymer of TiO2 with Phenylalanine as the seed molecule selected for its performance in increasing the sensitivity of the ion sensitive material 102 in detecting both Malic acid and Lactic acid concentrations in wine fermentations is a significant area of application of the invented method. Alternatively, the target ion of Malic acid may be used as a sol-gel seed molecule 304 in a TiO2 polymer in forming the imprinted sol-gel matrix 302 to enable the second invented sensor 300 to be especially sensitive to both Malic acid and Lactic acid concentrations in wine fermentations.

Figure 4:
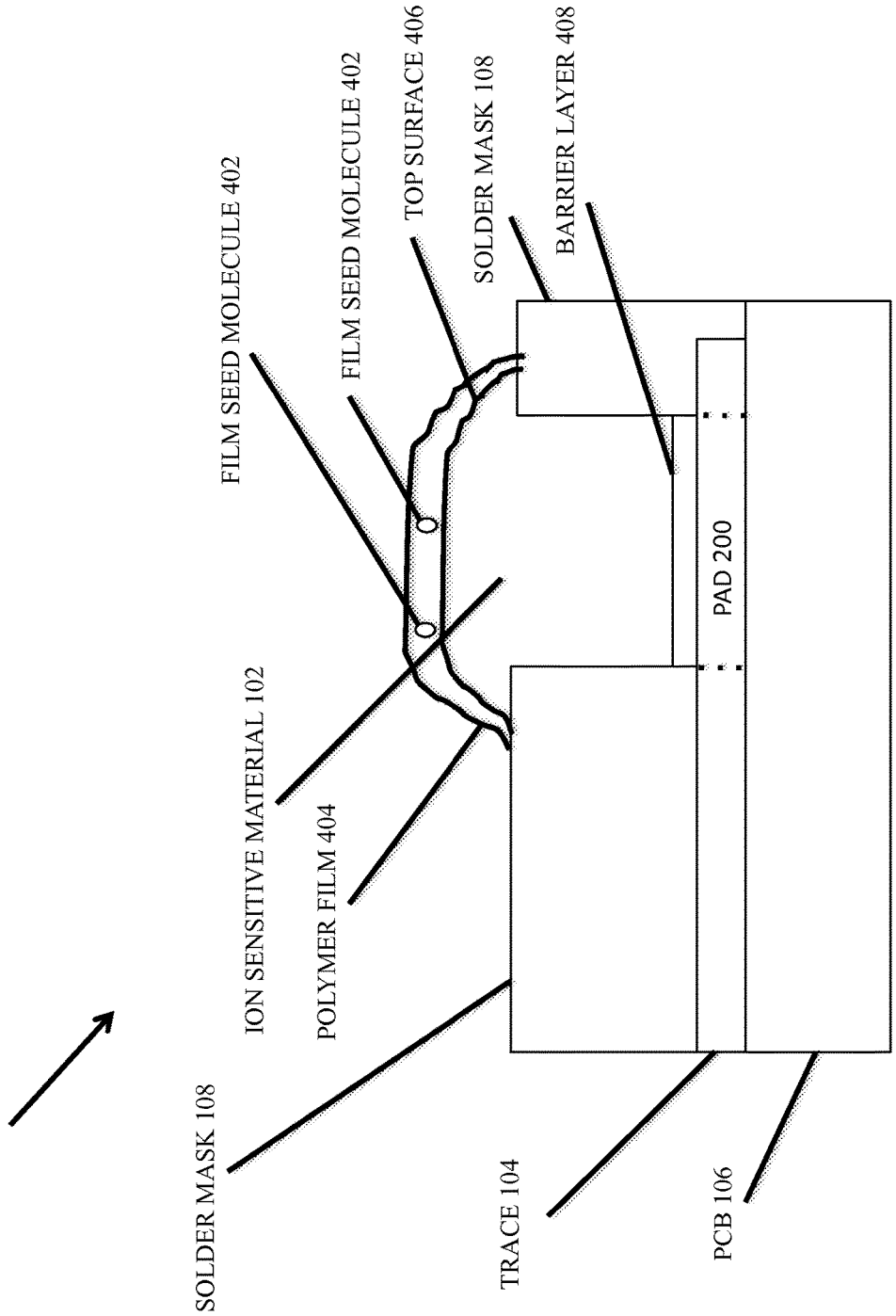
FIG. 4 is a detailed cut away side view of the invented sensor of the first version of FIG. 1 and illustrating the addition of a polymer film containing a plurality of film seed molecules, and an optional barrier layer.

Referring generally to the Figures and particularly to FIG. 4, FIG. 4 is a detailed cut away side view of a third invented sensor 400 that further comprises a plurality of film seed molecules 402 contained with a polymer film 404. The polymer film 404 is placed on a top surface 406 of the ion sensitive material 102 and is therefore disposed between the ion sensitive material 102 and any solution to be exposed to the third invented sensor 400.

An optional barrier layer 408 is positioned between the pad 200 and the ion sensitive material 102. The barrier material 408 may comprise graphene or another suitable material known in the art that impedes contamination of the ion sensitive material 102 sourced from the pad 200 and preferably presents a resistance to electrical current of less than one megaohm between the ion sensitive material 102 and the pad 200.

Figure 5:
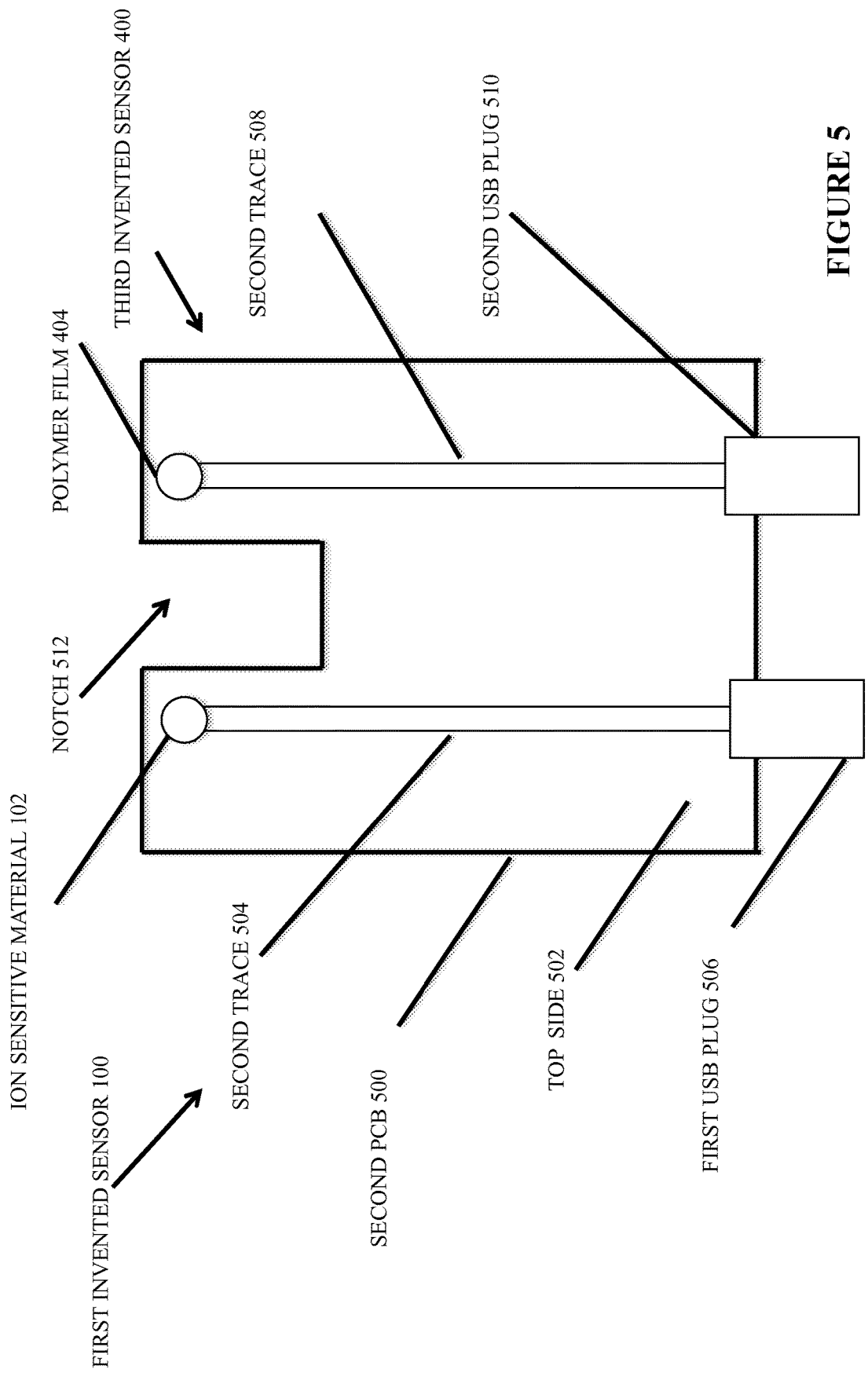
FIG. 5 is a top view of a variation of the present invention wherein the invented sensor of the first version of FIG. 1 and the invented sensor with a polymer film of FIG. 4 are both presented on a same printed circuit board.

FIG. 5 presents a second printed circuit board 500 (hereinafter "second PCB 500") in a view of the top side 502 of the second PCB 500. The first invented circuit 100 is formed with a second trace 504 that electrically couples the ion sensitive material 102 and an optional first Universal Serial Bus B Plug 506. Each Universal Serial Bus B Plug (hereinafter, "USB plug") is configured to deliver an electrical signal from an invented sensor 100, 300 & 400 to an off-board measurement instrument. The third invented circuit 400 is formed with a third trace 508 that electrically couples the ion sensitive material 102 (not shown) of the third invented circuit 400 with an optional second Universal Serial Bus B Plug 510.

A notch 512 of the second PCB 500 enables the first sensor 100 and the third sensor 400 to be more expeditiously manufactured by mechanically separating the respective ion sensitive material 102 of sensor 100 and the third sensor 400 during a sol-gel process.

Figure 6:
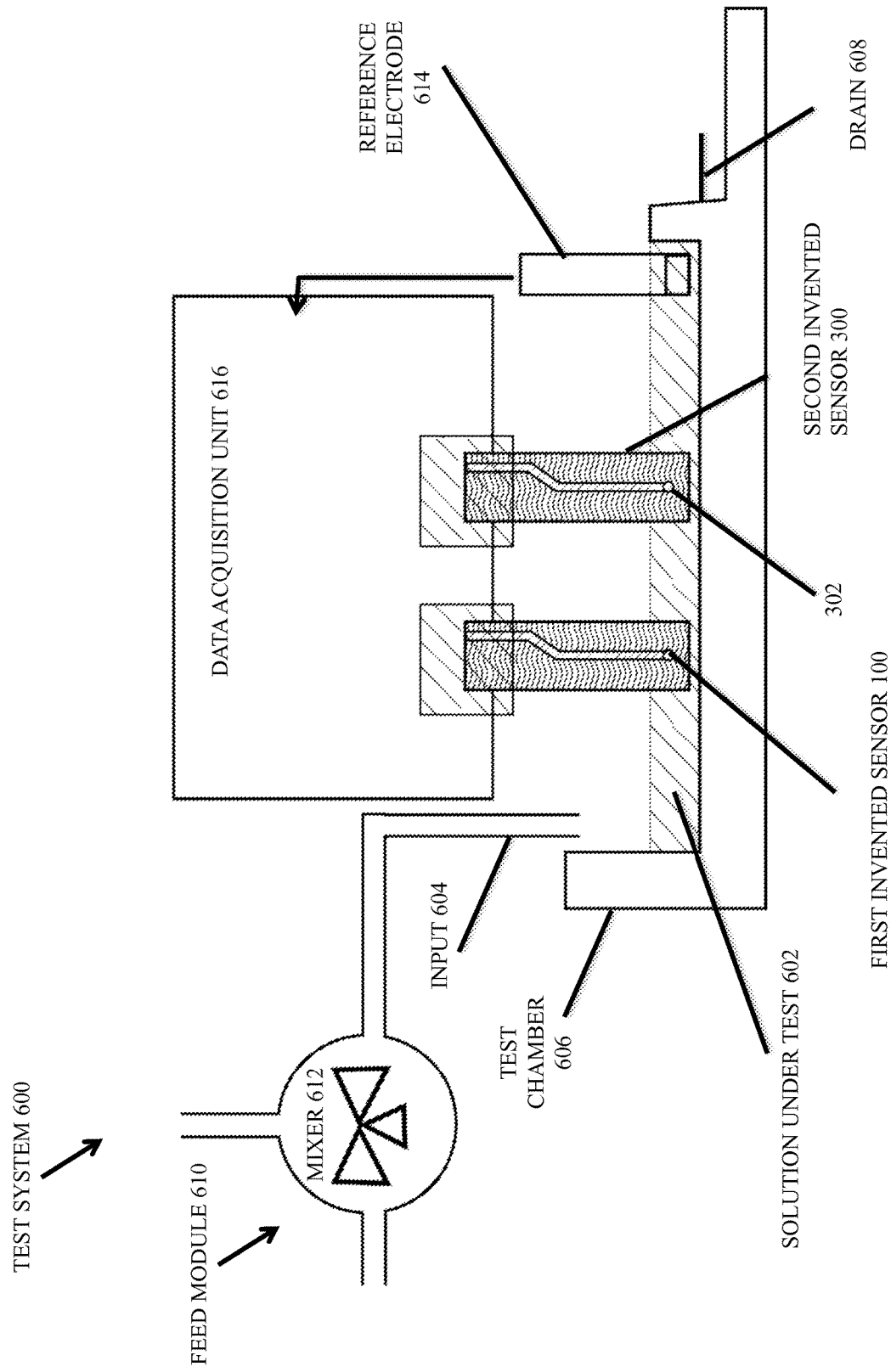
FIG. 6 is a block diagram of a test system of the invented sensor of FIG. 1 in contact with a solution under test.

Referring generally to the Figures and particularly to FIG. 6, FIG. 6 is a block diagram of an invented test system 600 that places two invented sensors 100 & 300 in contact with a solution under test 602. In the instant example of the invented method of FIG. 3, the first invented sensor 100. An input tube 604 delivers the solution under test 602 into a test chamber 606. A drain 608 provides an egress for the solution under test 602 from the test chamber 606.

A feed module 610 accepts liquid agents from reservoirs (not shown) into a mixer 612, wherein the liquid agents are mixed and passed through an input tube 604 and combined with the solution under test 602 within the test chamber 606. The two invented sensors 100 & 300 along with a reference electrode 614 are electrically coupled with a data acquisition unit 616 whereby the measured electrical potential of the first invented sensor 100, the second sensor 300 and the reference electrode 614 to determine a concentration of one or more target ions within the solution under test 602. The data acquisition 616 may be or comprise a FLUKE 8846A™ DMM digital multimeter marketed by Everett Wash. or other suitable electrical parameter measurement system known in the art.

The ion sensitive materials 102 of the respective invented sensors 100 & 300 are preferably submerged within the solution under test 602. It is understood that the reference electrode 640 might comprise silver, silver chloride, calomel and/or other suitable electrical potential materials known in the art. It is further understood that the reference electrode 640 might be or be enhanced with a pseudo reference electrode or quasi-reference electrode in alternate embodiments of the invented test system.

Figure 7A:
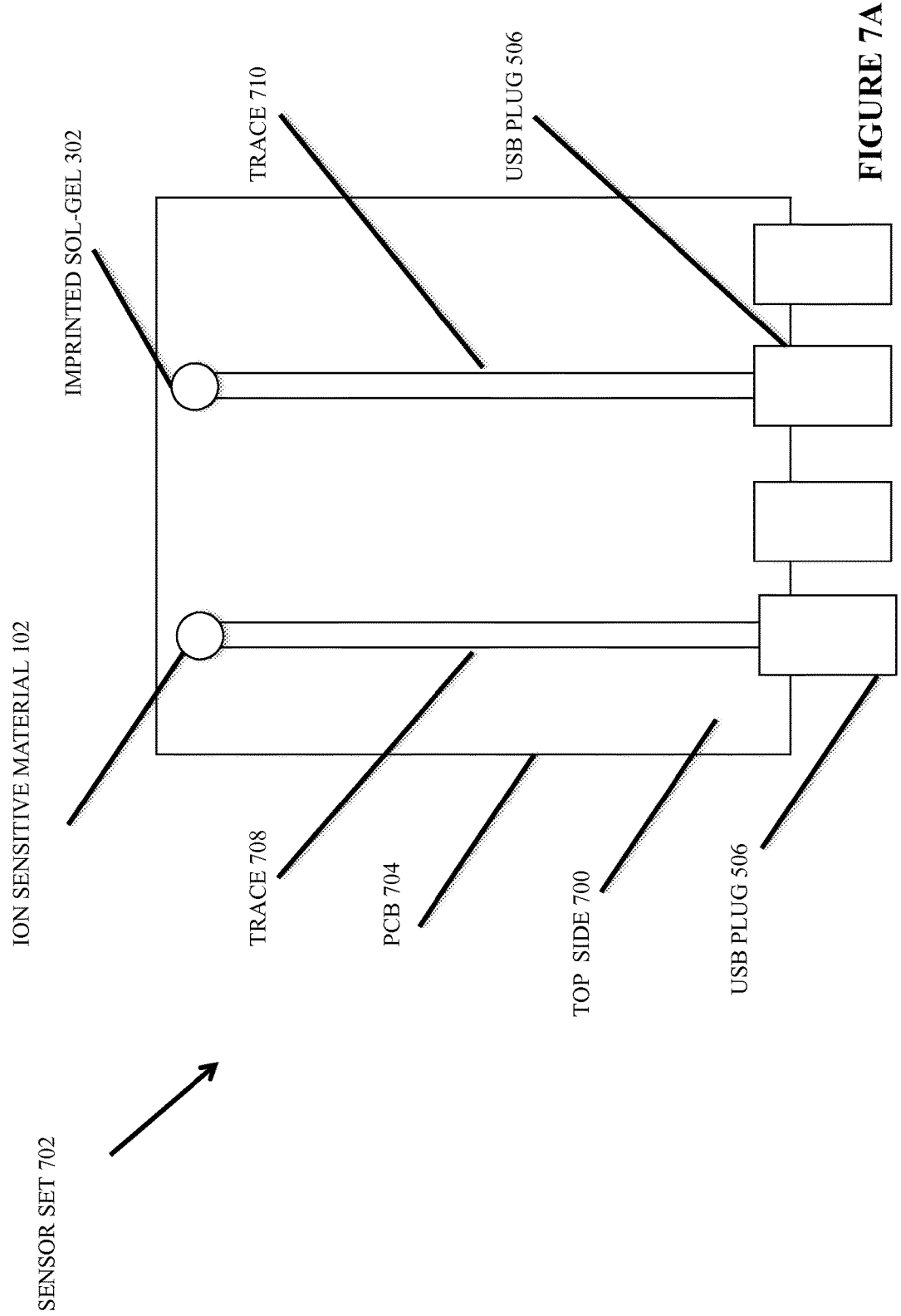
FIG. 7A is a front view of a variation of the present invention of FIG. 1 wherein four invented sensors are formed on a same printed circuit board with two sensors placed on each side of the alternate printed circuit board.

Referring generally to the Figures and particularly to FIG. 7A, FIG. 7A is a view of a front side 700 of a sensor set 702 that is an alternate embodiment of the present invention wherein four invented sensors 100, 300 & 400 are formed on an alternate printed circuit board 704 wherein two pairs of invented sensors 100 & 300, 100 & 400 are separately placed on alternate sides 700 & 706 of the alternate printed circuit board 704 (hereinafter, "PCB 704"). FIG. 7A shows a first pair of sensors 100 & 400 positioned on the front side 700 of the alternate PCB 704 wherein each first invented sensor 100 & 400 includes an alternate trace 708 & 710 that each lead from each respective ion sensitive material 102 to a dedicated USB plug 506.

Figure 7B:
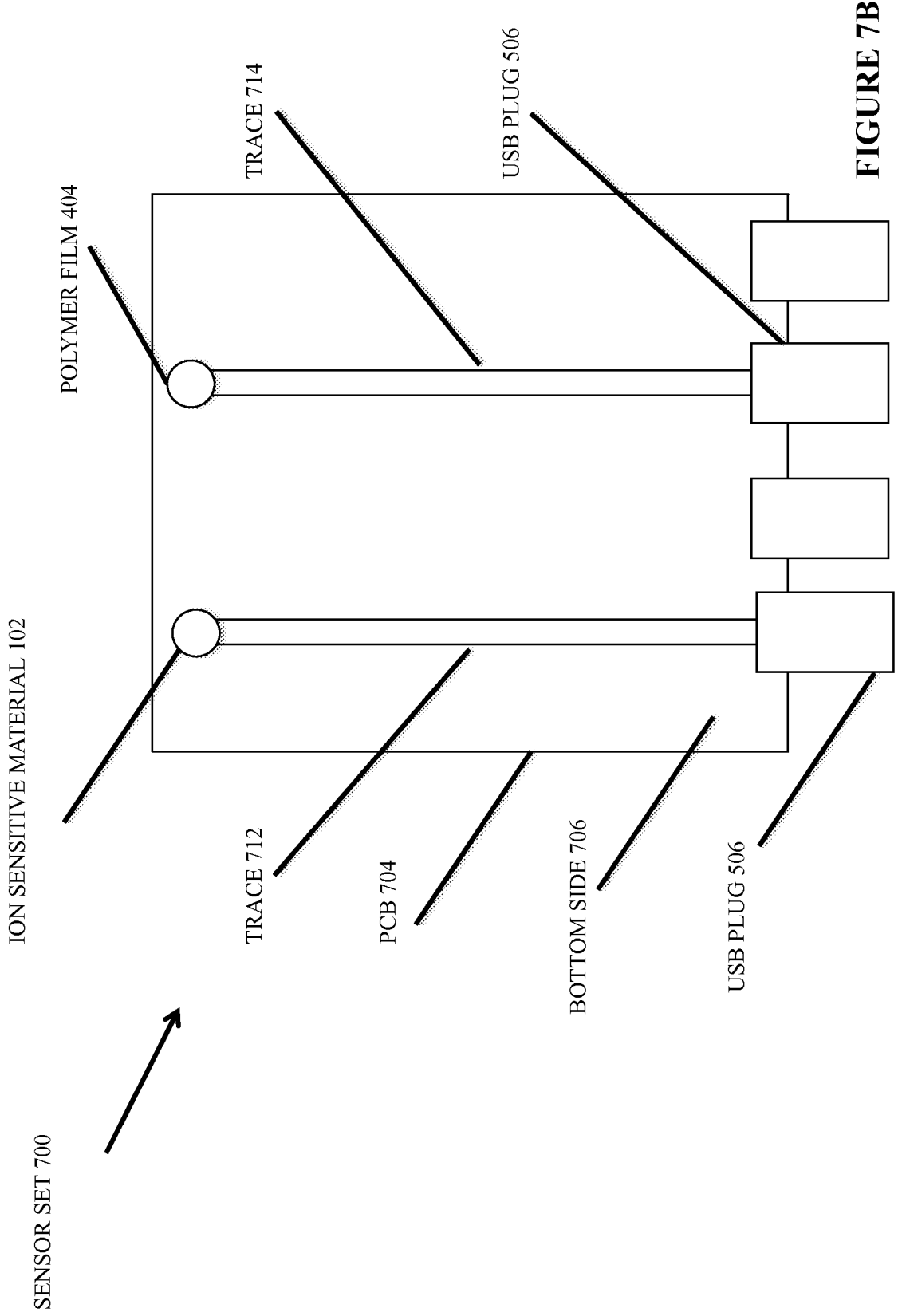
FIG. 7B is a back view of the alternate printed circuit board of FIG. 7A showing the two additional sensors.

Referring generally to the Figures and particularly to FIG. 7B, FIG. 7B is a back view of the alternate PCB 704 showing the two additional sensors 100 & 300. A third ion sensitive material 102 of the additional second invented sensor 300 has preferably been treated with a molecular imprinting process whereas a fourth ion sensitive material 102 of the first invented sensor 100 has not been molecularly imprinted. Each additional sensor 100 & 300 includes an alternate dedicated trace 712 & 714 that leads from each respective ion sensitive material 102 to a dedicated USB plug 506. It is understood that a barrier material 406 (not shown) may optionally disposed between both (a.) the third trace 712 and the ion sensitive material 102 of the first invented sensor 100 and/or (b.) the fourth trace 714 and the ion sensitive material 102 of the third invented sensor 400.

Figure 8:
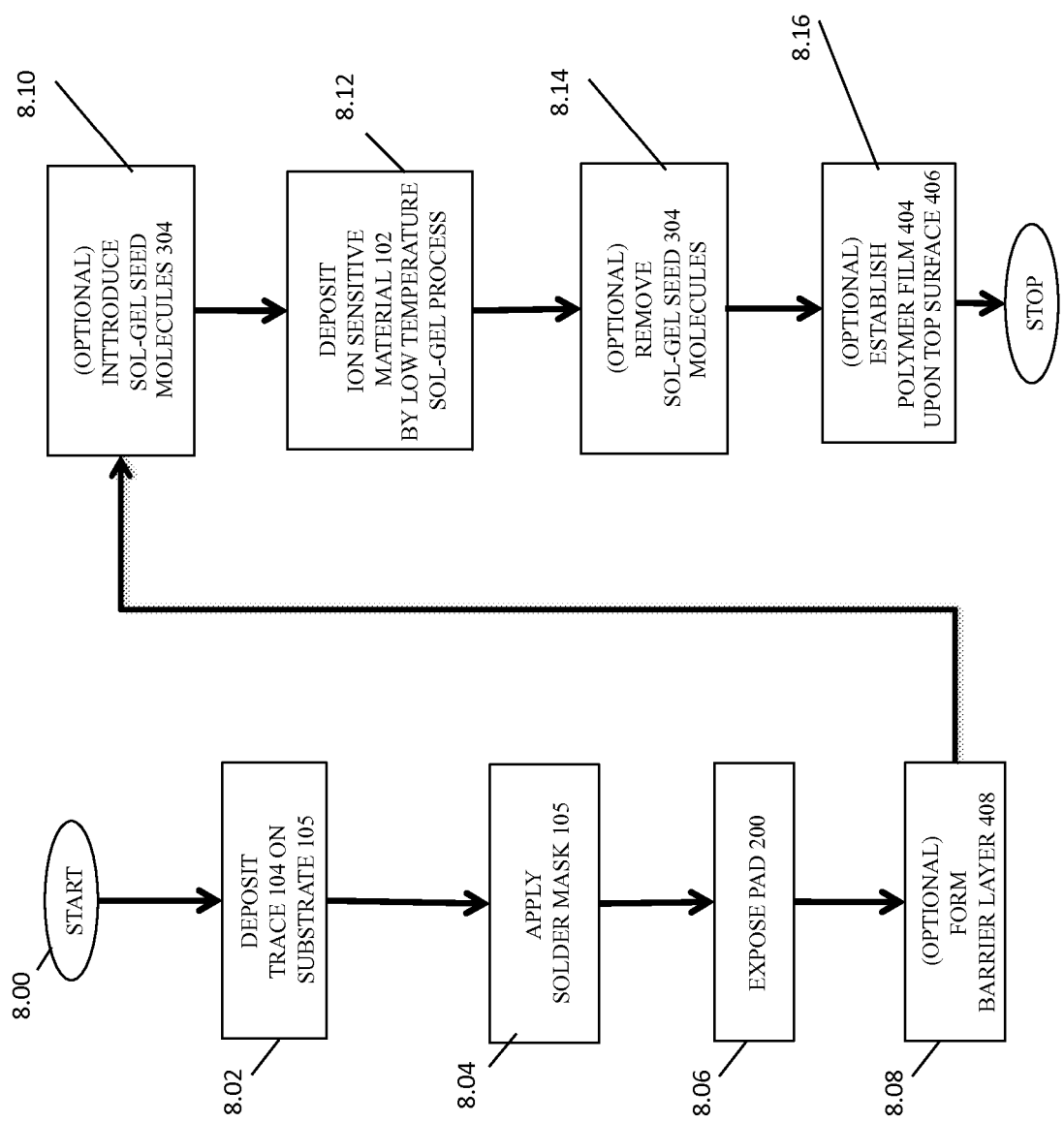
FIG. 8 is a process chart of a method of manufacturing the invented sensor of FIG. 1 on a printed circuit board.

Referring generally to the Figures and particularly to FIG. 8, FIG. 8 is a process chart of a method of manufacturing the invented sensors 100, 300 & 400 on the printed circuit board 106. It is understood that process steps 8.02, 8.04, and 8.06 are achievable through prior art PCB manufacturing processes, and that the process steps 8.08 through 8.16 provide novel and non-obvious inventive aspects. It is further understood that the manufacturing method of FIG. 8 may be applied to fabricate additional sensors 100, 300 & 400 with variations made obvious in light of the description of manufacturing the first invented sensor 100.

In step 8.02 the electrically conductive trace 104 with its pad 200 is formed on the nonconductive substrate 105 by prior art means. In step 8.04 the solder mask 108 is added over a top surface of the substrate 105 to enclose the trace 104 in combination with the substrate 105. In step 8.06 a volume of the solder mask 105 proximate to the pad 200 is removed whereby the pad 200 is exposed. The optional barrier layer 408 is formed upon the pad 16 in step 8.08. In optional step 8.10 sol-gel seed molecules 304 are introduced into the ion sensitive material 102 in a molecular imprinting process that is finalized in step 8.12.

The ion sensitive material 102 is deposited by a sol-gel process of step 8.12 that preferably does not exceed 200 degrees Celsius and more preferably does not exceed 100 degrees Celsius. In optional step 8.14 at least some of the sol-gel seed molecules 304 are removed from imprinted sol-gel matrix 302. In optional step 8.16 the polymer film 404 is established on the top surface 406 of the ion sensitive material.

There are many prior art process steps known in the art that may be adapted by one of ordinary skill in the art and in light of the present disclosure to fabricate the first invented sensor 100 and alternate invented sensors 300 & 400. For example, the alternate PCB 706 will require placement of traces 708, 710, 714 & 716 and two solder masks (not shown), as well as removal of the solder mask material from the pads 200 and optional depositions of barrier layers 408 and ion sensitive material 102 on alternate sides of the alternate PCB 404.

In exemplary process of depositing the barrier layer 408, offered by way of clarity of explanation and not limited to, the barrier layer 408 may comprise graphene and may be formed using graphene oxide that is sonicated in de-ionized water at 38 kHz for 8 hours. A reducing agent may be added to the graphene oxide solution, such as hydrogen peroxide, to help with exfoliating the graphene sheets. The sonicated graphene oxide can then be introduced by dipping the PCB 106 into a graphene bath, spinning a graphene delivery solution over the top surface of the PCB 106, casting or dropping the graphene onto the pad 200, or printed onto the pad 200 for preparation as the barrier layer 408. The graphene oxide can then be exposed to light to form the graphene barrier layer 408. In one optional aspect of the invented method, graphene as placed upon the pad 200 is exposed for 6 minutes to 253 nm light to form the barrier layer 408. In one optional preferred embodiment of the invented system, the sonicated graphene oxide is deposited in layers in two or more cycles and deposition and curing with ultraviolet light.

In a preferred embodiment, prior to applying the ion sensitive material 102 onto the pad 200 in step 8.12, the solder mask 108 is cleaned. Methods known to those skilled in the art may be applied for this cleaning such as dipping the surface into acetone solution and then flushing with de-ionized water.

Figure 9A:
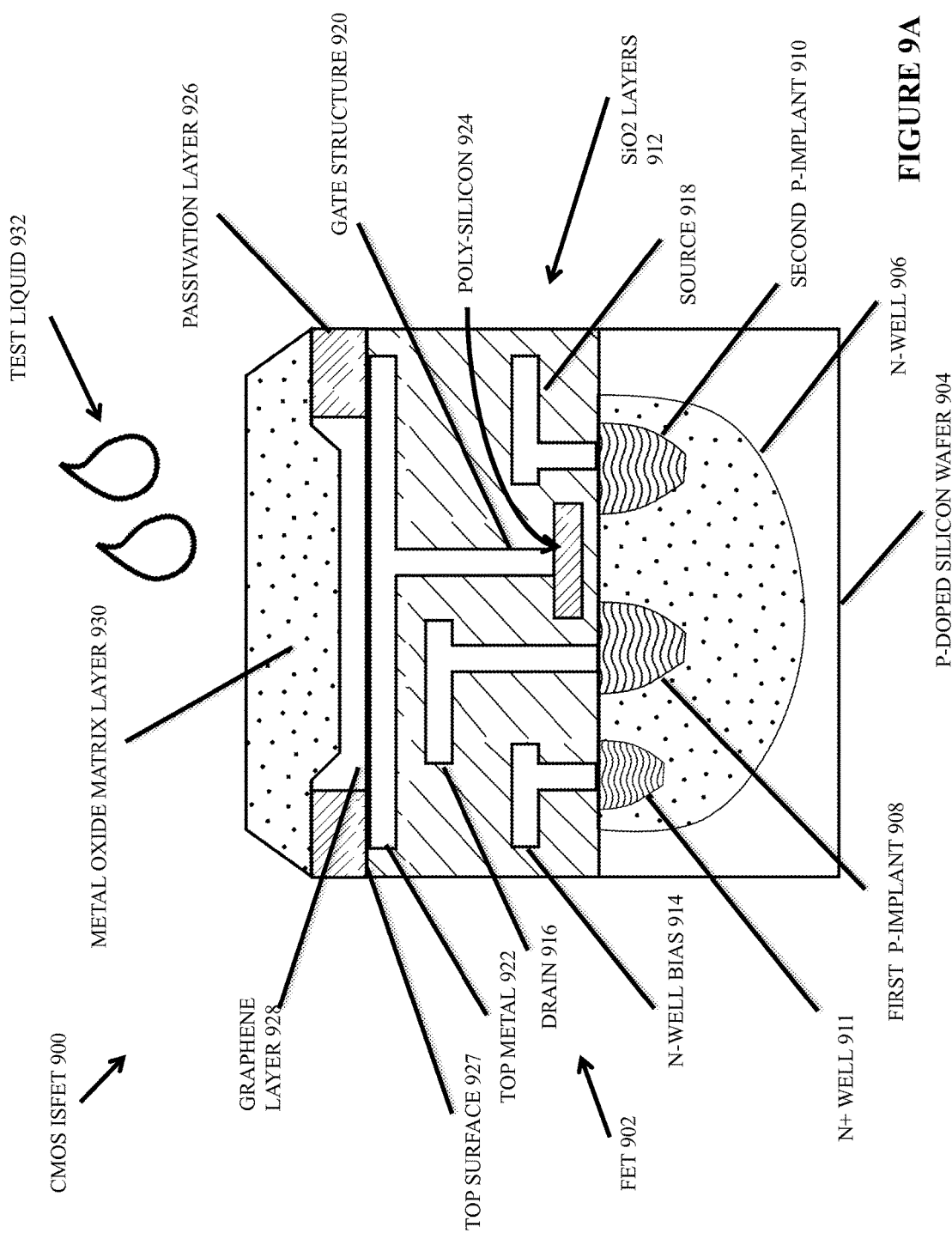
FIG. 9A is a cut-away side view of an alternate preferred embodiment of the present invention comprising a CMOS ISFET with a seeded sol-gel layer and an optional barrier layer.
Figure 9B:
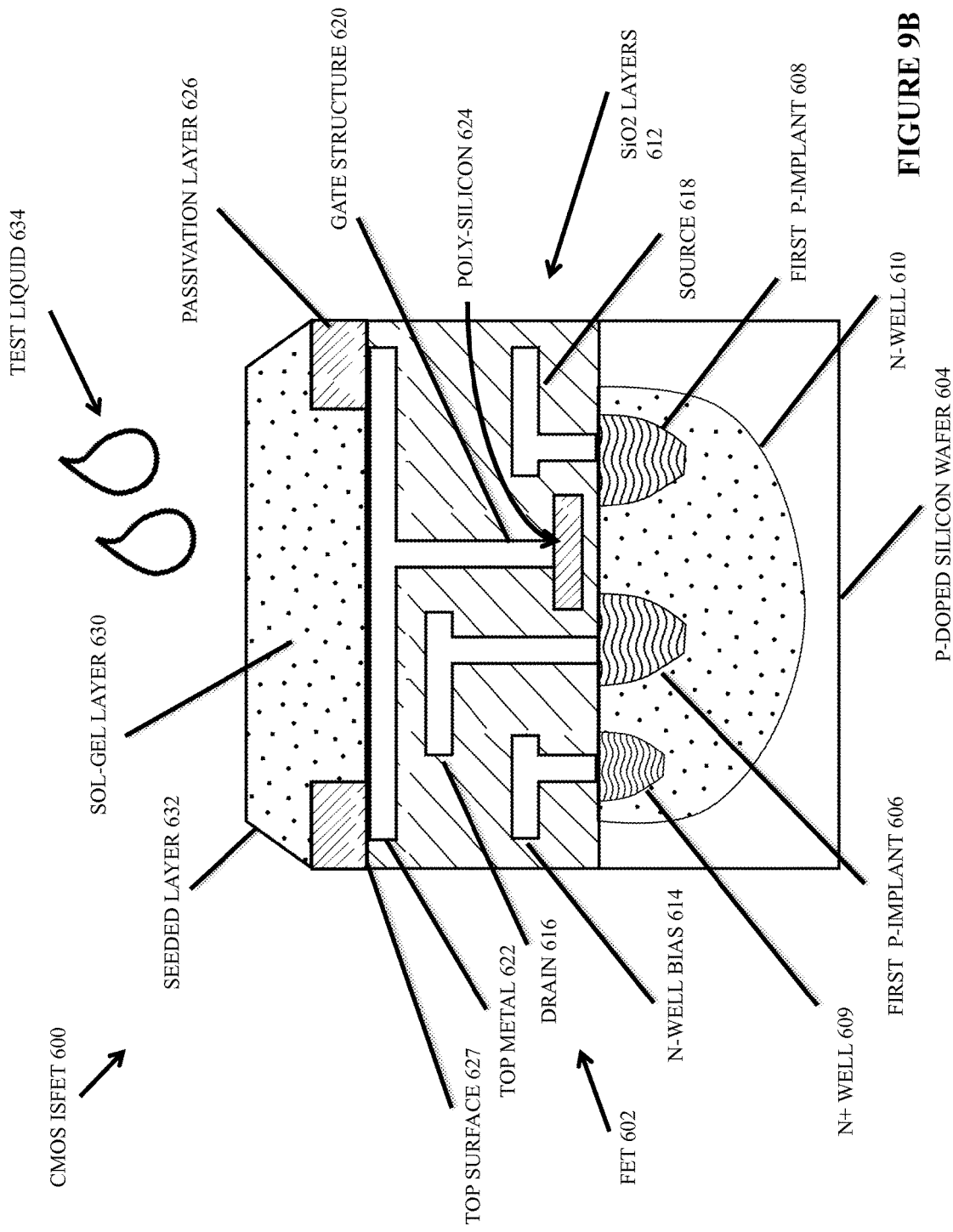
FIG. 9B is a cut-away side view of the CMOS ISFET of FIG. 9A with a seeded sol-gel layer and without the optional barrier layer.

Referring generally to the Figures and particularly to FIG. 9, FIG. 9 is a cut-away side view of an alternate preferred embodiment of the invented sensor comprising an invented CMOS ISFET 900 (hereinafter, "ISFET" 900"). The ISFET 900 comprises a field effect transistor structure 902 (hereinafter, "FET 902") that is built by CMOS fabrication technology upon a P-doped silicon wafer 904. It is understood that alternate preferred embodiments of the invented CMOS ISFET are alternately built with a CMOS N-FET or a CMOS P-FET.

An N-well 906 region with the silicon wafer 904 surrounds a first P-implant 908, a second P-implant 910 and an N+ well 911. The FET 902 is formed within a plurality of layers silicon dioxide 912, or other materials specific to the FAB house, that are successively layered upon the silicon wafer 904. The FET 902 comprises an N-well bias 914 that is positioned proximate to the N+ well 911, a drain 916 that extends from the first P-implant 908, a source 918 that extends from the second P-implant 910, and a gate structure 920 having a top metal layer 922. The gate structure 920 is coupled with a poly-silicon element 924, wherein the poly-silicon element 924 is positioned between the gate structure 920 and the silicon wafer 904. A passivation layer 926 resides on a top surface 927 of the silicon dioxide layers 912, wherein the passivation layer 926 is removed from over half of the FET top metal 922 to optionally enable a graphene barrier layer 928 to lay directly upon the FET top metal 922. A metal oxide matrix layer 930 preferably comprising a metal oxide and a plurality of sol-gel seed molecules 304 is positioned either upon the optional graphene barrier layer 928 or, when there is no barrier layer, directly upon the top metal 922. The metal oxide matrix layer 930 is preferably directly exposed to a test liquid 932.

The metal oxide matrix layer 930 is a resultant of molecular imprinting in conjunction with a molecular imprinting of a metal oxide with the plurality of sol-gel seed molecules 304. The metal oxide matrix layer 930 may include any of a number of suitable materials and suitable metal oxides known in the art that include Titanium, Tantalum, Vanadium, Aluminum, Silicon, Yttrium, Tin, one or more alloys of Lead and Titanium, Silicon Nitride, and/or other metals and alloys of suitable materials known in the art.

Figure 10A:
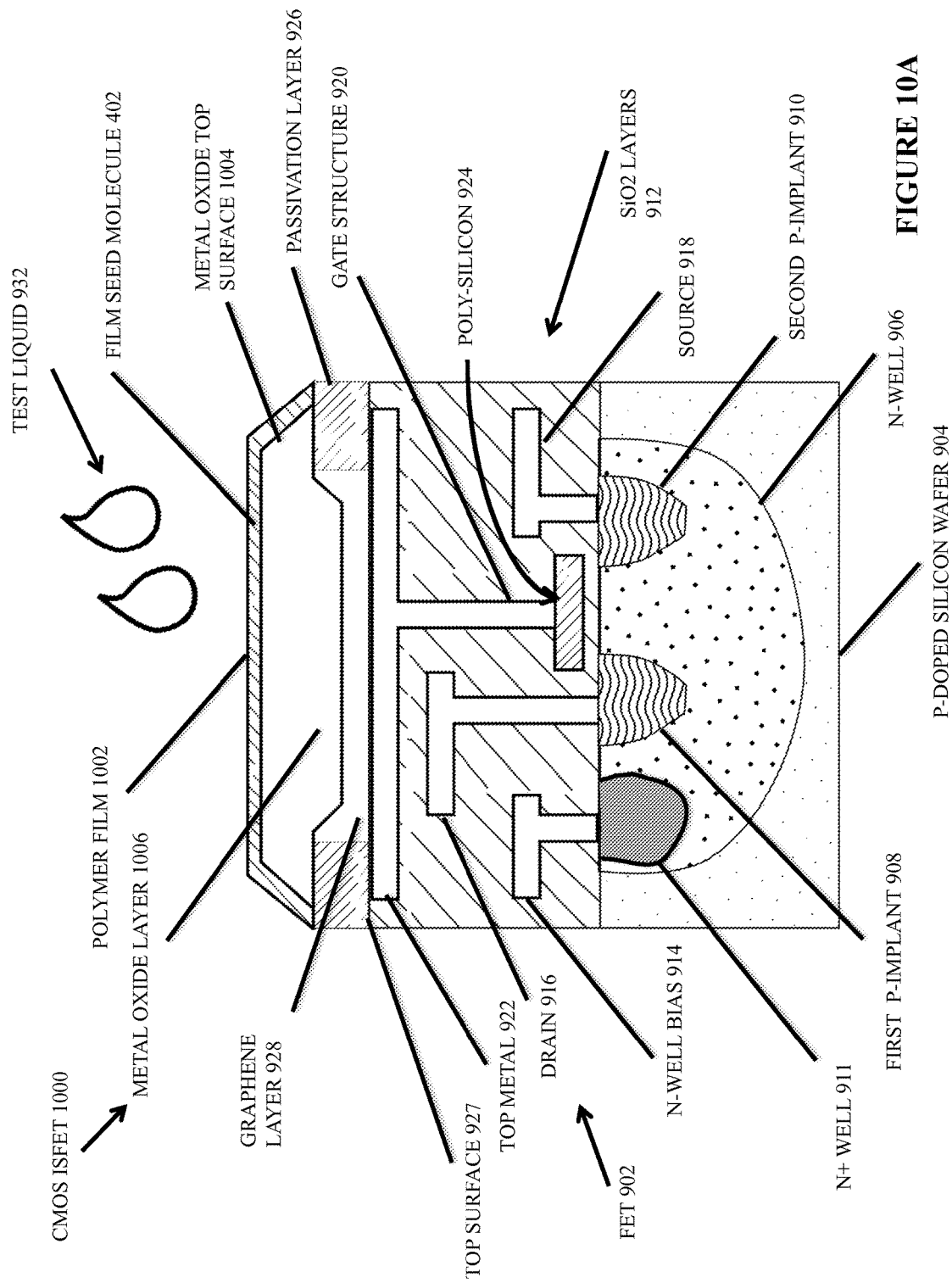
FIG. 10A is a cut-away side view of a still alternate preferred embodiment of the present invention comprising a CMOS ISFET with a seeded polymer film positioned on a top surface of a metal oxide layer.

Referring generally to the Figures and particularly to FIG. 10, FIG. 10 is a cut-away side view of a still alternate preferred embodiment of the present invention comprising a second CMOS ISFET 1000 comprising a seeded polymer film 1002 containing a plurality of film seed molecules 402 positioned on a top surface 1004 of a metal oxide layer 1006. The seeded polymer film 1002 is preferably directly exposed to a test liquid 932. Furthermore, in the alternate embodiment of the invented method wherein the second invented CMOS ISFET 1000 comprises a metal oxide layer 1006 with Titanium Dioxide by itself and without additional molecular imprinting or the addition of the film polymer 1002, the second invented CMOS ISFET 1000 is sensitive to, and may be applied to measure, concentrations of both Malic acid and Lactic acid in the test liquid 932.

In one example of another alternate preferred embodiment of the invented method applied to generate a CMOS ISFET that is sensitive to Potassium, the seeded polymer film 1002 surface may be cast from a THF solution in the following compositions: 10 mg valinomycin, 0.89 ml dioctyladipate, 0.33 g poly(vinylchloride), 13.0 ml tetrahydrofurane (THF). The process of depositing the polymer film 1002 may be conducted in a N2 chamber, with a mixture of the various components in a beaker with a stir bar. Aliquot the solution to the surface of the chips using a drip, print, or casting process.

The metal oxide layer 1006 may include any of a number of suitable materials and suitable metal oxide known in the art that include Titanium, Tantalum, Vanadium, Aluminum, Silicon, Yttrium, Tin, one or more alloys of Lead and Titanium, Silicon Nitride, and/or other metals and alloys of suitable materials known in the art.

Figure 10B:
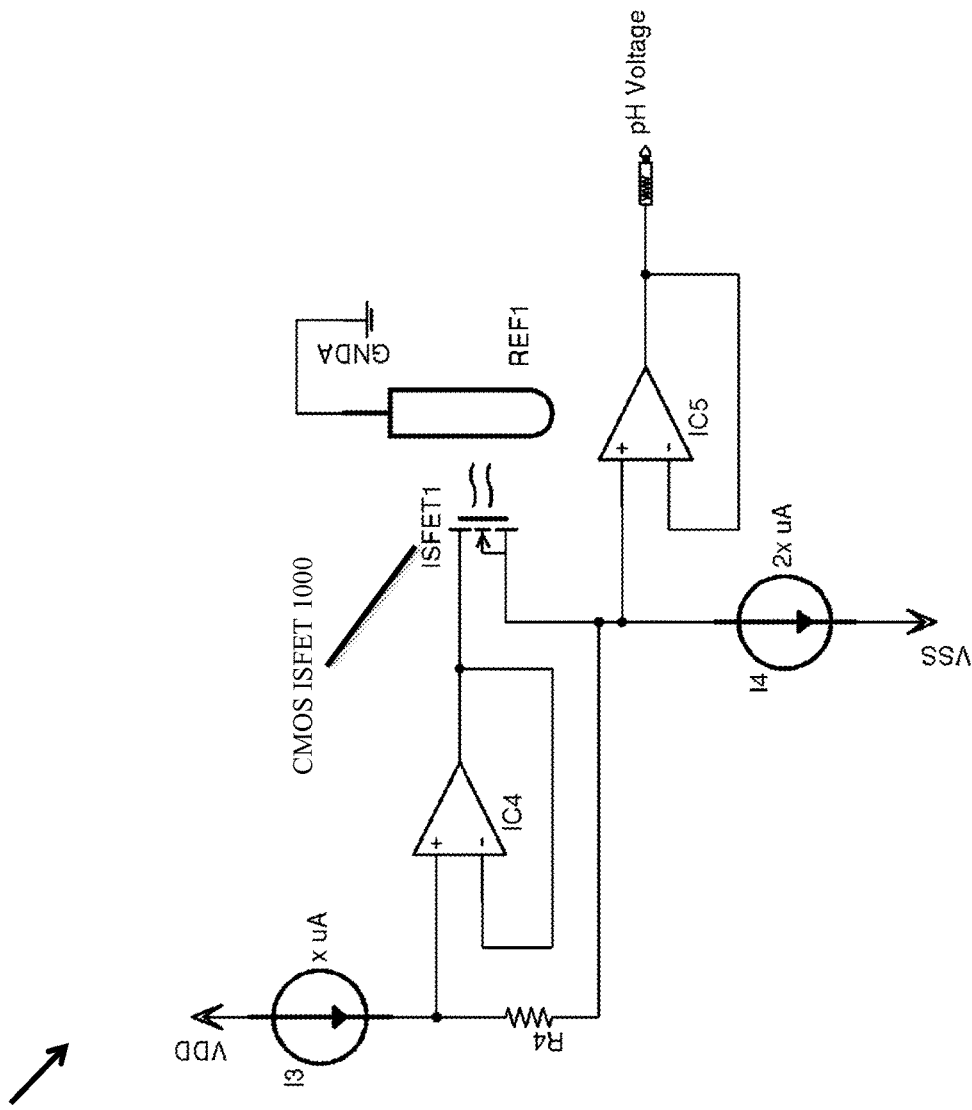
FIG. 10B is a circuit diagram of the CMOS ISFET of FIG. 10A in a circuit.

Referring generally to the Figures and particularly to FIG. 10B, FIG. 10B shows a biasing circuit 1008 configured and enabled for biasing and reading out an ISFET, e.g., the a second CMOS ISFET 1000. Circuit elements R4 and I3 set the voltage across the second CMOS ISFET 1000, while I4-I3 set the current flowing through second CMOS ISFET 1000. This dynamic of the biasing circuit 1008 keeps the second CMOS ISFET 1000 operating in a constant well defined state, meaning any substantive changes to the second CMOS ISFET 1000 are due to changes in charge at chemically sensitive metal oxide top surface 1004 of the second CMOS ISFET 1000. The IC5 buffers the voltage and tracks the change in charge on the chemically sensitive metal oxide top surface 1004 of the second CMOS ISFET 1000.

Unlike conventional ISFETs, all the circuitry of the biasing circuit 1008 can be incorporated onto the same die as the second CMOS ISFET 1000.

Figure 11:
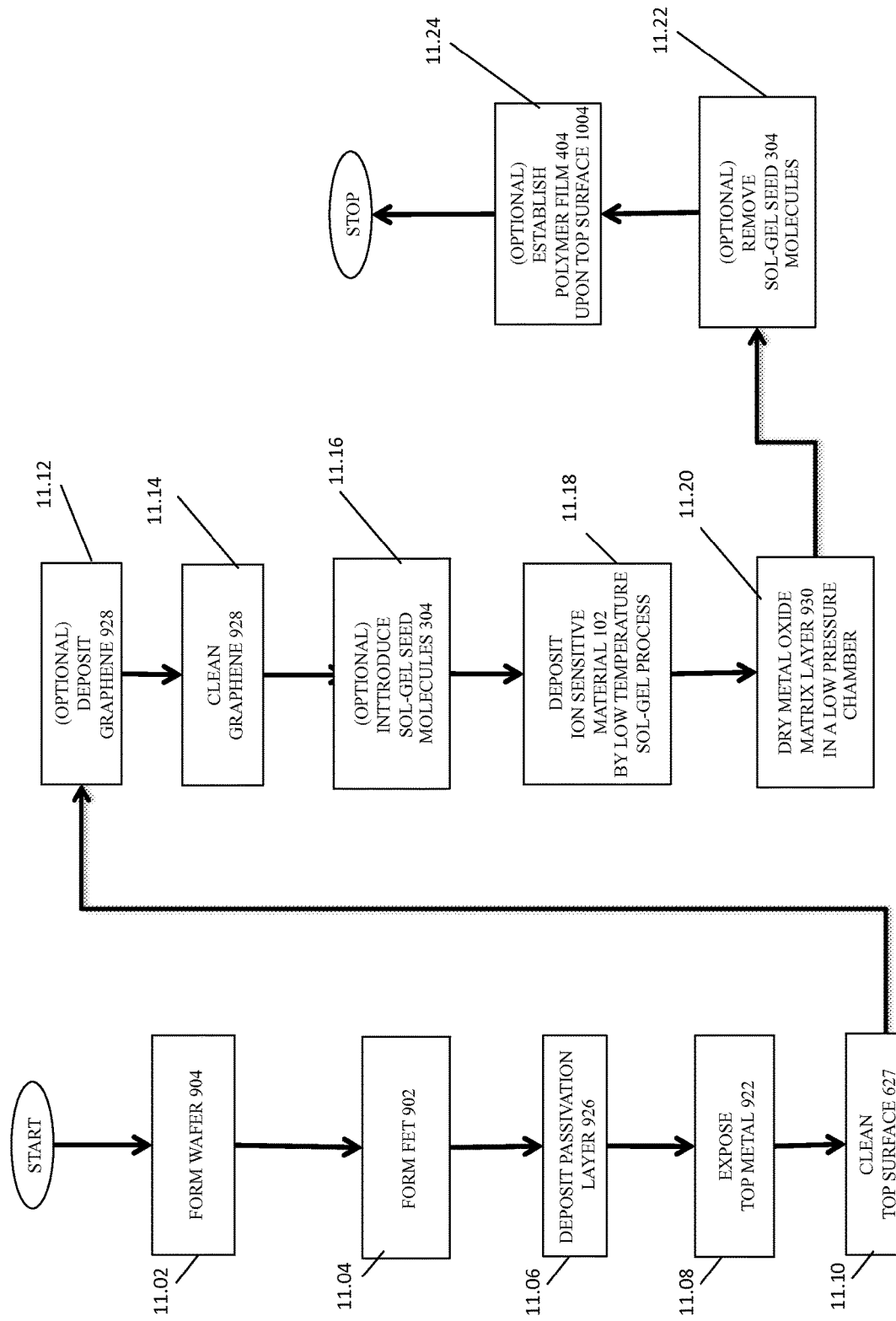
FIG. 11 is a process chart of a method of manufacturing the invented ISFETs of FIG. 9 or FIG. 10 that is in compliance with conventional CMOS fabrication technology.
Figure 12:
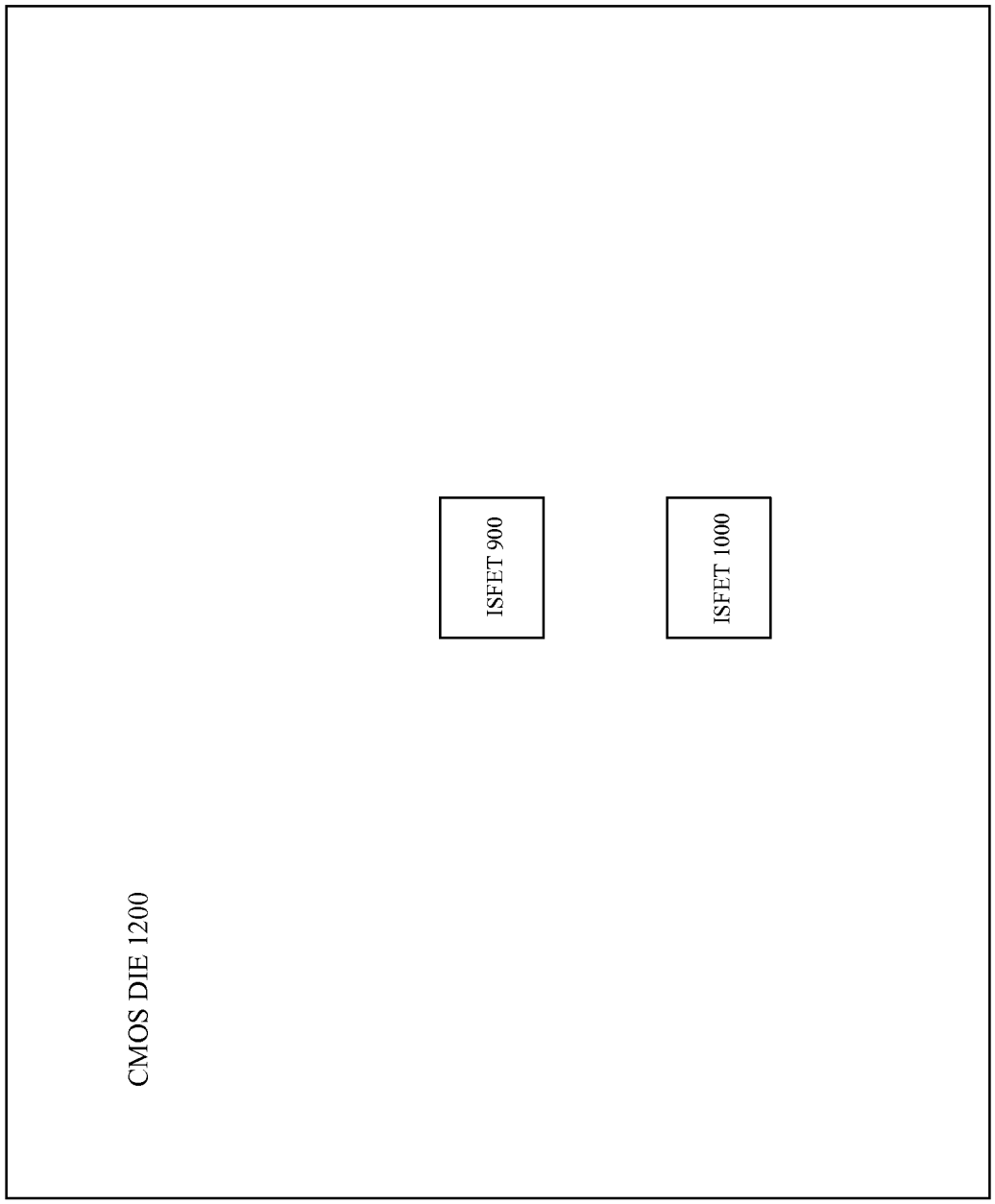
FIG. 12 is an illustration of two invented CMOS ISFETs on a same semiconductor die.

Referring generally to the Figures and particularly to FIG. 11, FIG. 11 is a process chart of a method of manufacturing the invented ISFETs of FIGS. 9 and 10 that is in compliance with conventional CMOS fabrication technology and preferably does not subject the FET 902 to temperatures above 200 degrees Celsius and more preferably does not subject the FET 902 to temperatures above 100 degrees Celsius. In step 11.02 the silicon wafer 904 is grown, sliced and doped, and the N-well 906, the first P-implant 908, the second P-implant 910 and the N+ well 911 are formed with the silicon wafer 904 by prior art techniques. In step 11.04 the FET 902 is formed preferably using prior art CMOS technology processes, and interconnects (not shown) within the silicon wafer 904 that carries electrical current to and from the drain 916 and the source 918 are added. The passivation layer 926 is added onto the silicon top surface 927 in step 11.06 and a volume of the passivation layer 926 is removed from the structure top metal 922 in step 11.08. The exposed top metal 922 is cleaned in optional step 11.10 and the optional graphene barrier layer 928 is formed in optional step 11.12.

The silicon wafer 904 and the FET 902 may be manufactured by conventional prior art CMOS device fabrication devices. The implant regions 906 through 911 of the silicon wafer 904 may be formed by ion implantation of charged p-type dopants and n-type dopants into silicon wafer 904. The silicon dioxide layers 912 may be formed by wet oxidation. Impurities are then implanted to form the N+ well bias 914, the drain 916, the source 918 and the gate structure 920 within the silicon dioxide layers 912 by well known methods of formation of FET elements, including mask set application techniques, diffraction grating techniques, spinning, dipping, mesotaxy, ion implantation, include physical vapor deposition, chemical vapor deposition, electrochemical deposition, molecular beam epitaxy, printing and other suitable semiconductor fabrication techniques known in the art.

The passivation layer 926 may be deposited by sputtering or other suitable semiconductor fabrication techniques known in the art. After a deposition of the passivation layer over and upon the top metal 922, the top metal 922 may be exposed to the graphene barrier layer 928, matrix oxide layer 930, or the metal oxide layer 1006 by removal of material of the passivation layer 926 by a grinding process, a polishing, a dry etch process, a wet etch process, a chemical-mechanical planarization, or other suitable material removal methods known in the art.

Interconnects (not shown) and insulating layers thereof that enable the drain 916 and the source 918 to receive and deliver electrical current are formed by conventional CMOS fabrication process known in the art, to include suitable deposition and removal techniques as known in the art.

It is understood that the optional barrier layer 928 may be graphene or another suitable material known in the art that is resistive to contamination or permitted passage of material from the top layer to the ion sensitive material. It is preferred that the selected material of the barrier layer 928 presents no more than approximately a megaohm of electrical current resistance between the top metal 922 and either the metal oxide layer 1006 or the metal oxide matrix layer 930.

The barrier layer top surface distal from the top metal 922 and the remaining passivation layer 926 may be cleaned in optional step 11.14. In optional step 11.16 sol-gel seed molecules 304 are introduced into the ion sensitive material 102 in a molecular imprinting process that is finalized in step 11.18 to produce the seeded sol-gel layer 930.

The process of FIG. 11 preferably does not exceed subjecting the invented CMOS ISFETS 900 & 1000 to more than 200 degrees Celsius and more preferably does not apply more than 100 degrees Celsius to either the invented CMOS ISFET 900 & 1000 at any point. In optional step 11.20 the metal oxide matrix layer 930 is dried in a vacuum chamber preferably in a gaseous environment of less than 0.5 Atmospheres. For example, drying the metal oxide matrix layer 930 using a glass jar equipped with a suitable vacuum pump will provide the required vacuum chamber.

In optional step 11.22 at least some of the sol-gel seed molecules 304 are removed from imprinted seeded sol-gel layer 930. In optional step 11.24 the polymer film 404 is established on the top surface 1004 of the ion sensitive material 102, i.e., the metal oxide.

It is understood that seeded and sensitized metal oxide matrix layer 930 comprising. Molecular Imprinted Polymers provide a very flexible, general purpose mechanism for the detection of chemical species. These polymers can be fabricated to exhibit with good selectivity and sensitivity to a large variety of organic molecules and even bacteria.

One significant advantage to the invented ISFET 900 having a seeded sol-gel layer 930 comprising TiO2 is increased sensitivity to other chemical targets other than pH. Sol-gel seed molecules 304 alternately used to form the seeded sol-gel layer 930 include 3-Amino-2-hydroxy-3-phenyl-propionic, Phenylalanine, b-Phenyllactic acid, 2-4D, Aspirin, Caffeine, 4-ethylphenol, Lactic acid and Malic acid. More particularly, the seeded sot-gel layer 930 of a first ISFET 900 may be generated with Phenylalanine as a sol-gel seed molecule 304, and the seeded sol-gel layer 930 of an alternate ISFET 900 may be generated with Malic acid as a sol-gel seed molecule 304. When the first ISFET 900 and the alternate ISFET 900 are simultaneously exposed to a same fermenting wine solution, the first ISFET 900 exhibits a slightly stronger and slower response to Lactic acid, whereas the alternate ISFET 900 with Malic acid seeding will show a stronger and slightly slower response to Malic acid.

Between these two ISFET sensors 900 one can derive an effective test for the Malic/Lactic acid ratio in a solution of wine.

One embodiment for the construction of the sol-gel layer 930 with TiO2 is as follows. A precursor Titanium (IV) Butanol is mixed in with equal parts toluene and butanol in a total volume of 10 ml. This solution is mixed until homogenous, at which time 400 µl of HCl and 100 µl of $H_2O$ are added under vigorous stirring. This solution is mixed within a closed boro-silicate vessel at ambient temperature for a 24 hour time period.

Deposition of multiple layers of titanium dioxide can improve performance and prevent liquid from drilling through the seeded sol-gel layer 930 and coming into contact with the top metal 922 or barrier layer 928.

One alternate embodiment of the invented method is to use the sol-gel process in the following way. A typical preparation is as follows, the precursor Titanium (IV) Butanol is mixed in with equal parts toluene and butanol in a total volume of 10 ml. This process employs the formation of a complex resulting from non-covalent or metal ion coordination interactions. This complex is formed by incubating the template within the seeded sol-gel layer 930 prior to the initiation of acid-catalyzed hydrolysis and condensation reactions. It is understood in the prior art that Sol-Gel metal oxide layer(s) may be composed and applied to detect a variety of ions and small molecules, including but not limited to: Table B.

It is further understood that it is not required to use the Sol-Gel method to form molecularly imprinted polymers. Other method step embodiments include methods such as polymerization, self-assembling peptides, Langmuir films, and self-assembled monolayers. These methods can be used to generate a polymer film over the metal oxide layer 1006 which are sensitive to other molecular targets.

Regarding the polymer film 1002 of the second invented CMOS ISFET 1000, the channels created by film seed molecules 402 are typically most suited for increasing sensitivity to small ions, such as SO2−, H2S, Ca+, K+, and Na+.

Figure 13:
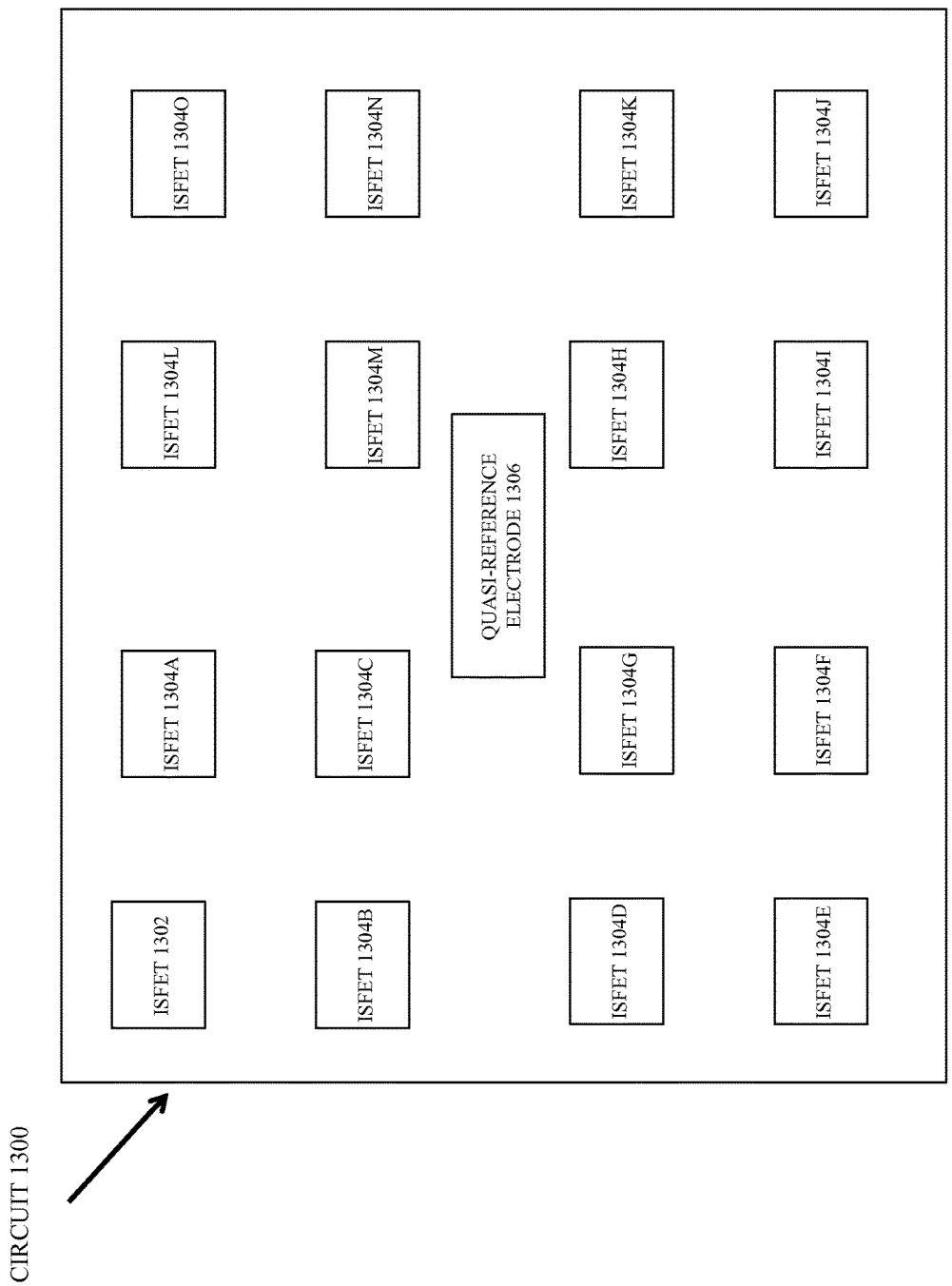
FIG. 13 is a top view of a CMOS circuit that comprises a plurality of sixteen invented CMOS ISFETs manufactured in accordance with the method of FIG. 7.

Referring now generally to the Figures and particularly to FIG. 13, FIG. 13 is a top view of a CMOS die 1200 that comprises both the first invented CMOS ISFET 1000 and the second invented CMOS ISFET 1000.

Referring now generally to the Figures and particularly to FIG. 13, FIG. 13 is a top view of a CMOS circuit 1300 that comprises a plurality of a third invented CMOS ISFET and fifteen CMOS ISFET's 1304A-1304O manufactured in accordance with the method of FIG. 11. The third invented ISFET 1302 has not been processed through step 7.18 or 7.20 and therefore has no sol-gel seed molecules 304 or polymer film 404 and merely presents an exposed metal oxide to a solution under test 602, whereas as each of the additional fifteen CMOS ISFETS 1304A-1304O have been either molecularly imprinted with a unique sol-gel seed molecule 304 or include a polymer film 404, whereby the CMOS circuit 1300 may detect at least fifteen target ions with greater specificity.

A variety of possible film seed molecules 402 for use in generating the polymer film 404 are presented in Table A.

TABLE A

| Film Seed Molecules | Detects | Comments |
| --- | --- | --- |
| Calcimycine | $Mn^{2+}$ | Works well with 2+ type cations, including $Ca^{2+}$ and $Mg^{2+}$. Some selectivity to $Sr^{2+}$ and slight selectivity for $Ba^{2+}$. |

TABLE A-continued

| Film Seed Molecules | Detects | Comments |
|---|---|---|
| Beauvericin | $Ca^{2+}$, $Ba^{2+}$ | |
| Carbonyl cyanide m-chlorophenyl hydrazone (CCCP) | $H^+$ | Pretty deadly stuff. |
| Enniatin | Ammonium | Nice ammonium detector. |
| Gramicidin A | $H^+$, $Na^+$, $K^+$ | |
| Ionomycin | $Ca^{2+}$ | |
| Lasalocid | Dopamine, monovalent and divalent cations | A nice example of a film seed molecule helping to detect larger molecules. |
| Monensin | $Na^+$, $H^+$ | Also useful for $Li^+$, $Na^+$, $K^+$, $Rb^+$, $Ag^+$, and $Ti^+$. |
| Nigericin | $K^+$, $H^+$, $Pb^{2+}$ | Combined with other film seed surfaces, this target allows one to detect lead. |
| Nonactin | ammonium ionophore I | |
| Nystatin | Ergosterol | This film seed molecule could allow the detection of certain fungi by binding to Ergosterol. Nystatin binds to Ergosterol, causing potassium to leak out of the fungi cells. Ergosterol is rare outside of fungi. |
| Salinomycin | $K^+$ | This target could be very useful for detecting cancer cells. In a study that screened 16,000 different chemical compounds, it was found that only a small subset, including salinomycin and etoposide, targeted cancer stem cells responsible for metastasis and relapse. |
| Valinomycin | potassium ionophore I | This is a standard antibiotic that is used for detection of potassium. It is highly selective over sodium. |
| Cryptands | varies | There are a range of these synthetic film seed molecules. A specific example would be 2.2.2-Crypt and and $K^+$. |
| Crown ethers | varies | There are a range of these synthetic film seed molecules. A specific example would be 18-crown-6 binding with $K^+$. |
| Calixarene | Varies | There are a range of these molecule that have been used in ion sensitive electrodes or sensors, selective membranes, non-linear optics. |
| Siderophores | $Fe^{3+}$ | |

Furthermore, the following Table B indicates classes of compounds of which ISFET 900 and ISFET 1000 may be adapted by molecular imprinting of the sol-gel seed molecules 304 to detect. It is understood that these adaptations presented in Table B may be affected by one of ordinary skill in the art in light of the present disclosure.

TABLE B

| Class of compound | Target Ions May Be Used as Sol-Gel Seed Molecules |
|---|---|
| Ions and salts | potassium, iron, magnesium, ammonium, nitrates, lead, sulfur, zinc, nickel, chlorine, copper manganese, molybdenum, phosphorus, nitrogen, phosphorus |
| Simple carboxylic acids | acetic, Lactic, Malic, citric, tartaric, beta-hydroxybutyric acid |
| Amino acids | monosodium glutamate, glycine, alanine, valine, leucine, isoleucine, serine, cysteine, selenocysteine, threonine, methionine, proline |
| Hormones | epinephrine, prolactin, acth, oxytocin. vasopressin, insulin, testosterone, 17-hydroxyprogesterone, cortisone, cortisol, estradiol, calcitriol, dopamine |
| Auxins | 2-4d, pesticides, indole-3-acetic acid, 2-phenylacetic acid, indole-3-butyric acid, 4-chloroindole-3-acetic acid, 1-naphthaleneacetic acid, 2,4,5-trichlorophenoxyacetic acid |
| Pesticides | see auxins, glyphosate |
| Phytohormones | abscisic acid |
| Cytokinins | zeatin, kinetin, 6-benzylaminopurine, diphenylurea, thidiazuro |
| Other plant hormones | brassinolide, salicylic acid, gibberellic acid |
| Ketones | acetoacetic acid, acetone |
| Globins | myoglobin, hemoglobin |
| Drugs | cocaine, nicotine, caffeine, psilocybin, 2,5-dimethoxy-4-bromoamphetamine, mdma, ketamine, salvinorin a, oxycodone, paracetamol, hydrocodone . . . |

TABLE B-continued

| Class of compound | Target Ions May Be Used as Sol-Gel Seed Molecules |
|---|---|
| Sugars | sucrose, glucose, galactose, fructose |
| Carbohydrates | lactose, maltose, inulin, cellulose |
| Fertilizers | see ions and salts |
| Antigens | hydralazine |
| Enzymes | creatine kinase |
| Aldehydes | acrolein |

The invented method has applications in numerous markets, including the markets specified in the following Table C,

TABLE C

| Market | Application | Comments |
|---|---|---|
| Medical | Blood glucose meter | Competitor to standard blood glucose meters for diabetic patients. |
| | Dialysis | Active management of electrolytes could lead to faster and better dialysis. Also by increasing the performance and safety, could lead to more home based machines. |
| | Kidney health | Monitor kidney health of patients. This could be placed in toilets or be a stick people urinate onto. For babies and older folks this could be embedded into a special diaper. |
| | Liver monitoring | Similar to kidney health, but probably in the toilet this time. |
| | Heart attack monitoring | Looking for proteins signaling muscle damage and possible onset of heart attack. System could provide quick feedback and cellular alerts for the problem. |
| | Breast milk analyzer | Lets lactating women monitor the nutrition of their breast milk, as well as checking that no dangerous drugs are present, such as alcohol. |
| | Alternative health meter | Useful for people who want to measure the in-vogue items in alternative medicine such as pH and minerals. Can provide advice and up-sell capability depending on what is measured. |
| | Allergen detector | Useful for people who have severe allergies. Could allow them to detect allergens in food at restaurants before they eat it. Also could be used for detection of caffeine and msg. |
| | Diet aid | Monitoring the burning of fat and current carb levels. Ties to social media would allow people to post on the fly and update their friends on the diet progress. |
| | Drug tester | People looking to test teens or workers for their use of controlled substances. |
| | Ovulation/pregnancy testing | Couples, or women, looking to get pregnant could use such a device to measure their hormones, temperature, and viscosity to improve the chance of fertilization. |
| | Cancer monitoring | Looking for antibodies and chemical markers of a relapse of cancer. |
| Water | Tap water tester | Looking to check for unsafe chemicals entering your water supply. Data can be aggregated into crowd sourced health maps, allowing home owners and renters to potentially identify local polluters. |
| | Grey water monitor | Allows for more efficient use of water. Careful monitoring could direct safe water to holding tanks for reuse in watering or other functions. |
| | Aquarium controller | Attempts to adjust and maintain aquariums in peak condition. |
| | Waste water treatment | Check that waste water can be discharged without concerns. |
| | Watershed manager | Allow the mapping of watershed health and concerns. Potentially identify polluters before they become a major problem. Shut down beaches or rivers before a "red tide" becomes a health hazard. |
| | Swimming pool/hot tub robot | Floating robot in your pool that adjusts chemicals to maintain pool in ideal health. Can be controllable from your cell phone, and communicate with other pools to know what problems are developing in the local community and determine what actions to take to help pools from turning into a green monster. |

TABLE C-continued

| Market | Application | Comments |
| --- | --- | --- |
| Agricultural | Soil manager | Looking for mineral levels in soil. Can detect the presence of harmful pests. |
| | Plant leaf tester | Allow accurate measurement of the uptake of fertilizer and nutrients. Alert growers of incoming pathogens that are attacking plants. |
| | Product tester | Monitor the health of high value crops from field to table. Usable by consumers, distributors, and stores to ensure good quality and no dangerous contaminants in packs of fresh vegetables, fruits, and salad greens. |
| | Smart bung wine analyzer | Monitor the health and aging of wines in the barrel. This is the initial market we are targeting, |
| Industrial | Process control | Replace existing chemical sensors, mainly pH and ISE probes. |
| Livestock | Health monitor | Look for nutrition and health issues in livestock. Allow for localized application of antibiotics and other drugs, as well as segregation of sick animals. |
| Pets | Health monitor | For cats, sensors could be added to litter and their signals picked up by using a special litter tray. This can measure a mammalian pet's health like a kidney and liver monitor. |
| Gas and Oil | Waste treatment and recovery | Helping oil services companies manage oil extraction. Using remote sensing to ensure safe and proper disposal of oil and gas well waste. |
| Athletes | Triathlete, performance athlete enhancer | Determine if athletes are burning fat or muscle. Look at how effectively the liver is converting fat to energy. Examine the mineral and glucose level in the blood for deficiency and effectiveness of an exercise program. |

The foregoing description of the embodiments of the invention has been presented for the purpose of illustration; it is not intended to be exhaustive or to limit the invention to the precise forms disclosed. Persons skilled in the relevant art can appreciate that many modifications and variations are possible in light of the above disclosure.

Seine portions of this description describe the embodiments of the invention in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

Any of the steps, operations, or processes described herein may be performed or implemented with one or more hardware or software modules, alone or in combination with other devices. In one embodiment, a software module is implemented with a computer program product comprising a non-transitory computer-readable medium containing computer program code, which can be executed by a computer processor for performing any or all of the steps, operations, or processes described.

Embodiments of the invention may also relate to an apparatus for performing the operations herein. This apparatus may be specially constructed for the required purposes, and/or it may comprise a general-purpose computing device selectively activated or reconfigured by a computer program stored in the computer. Such a computer program may be stored in a non-transitory, tangible computer readable storage medium, or any type of media suitable for storing electronic instructions, which may be coupled to a computer system bus. Furthermore, any computing systems referred to in the specification may include a single processor or may be architectures employing multiple processor for increased computing capability.

Embodiments of the invention may also relate to a product that is produced by a computing process described herein. Such a product may comprise information resulting from a computing process, where the information is stored on a non-transitory, tangible computer readable storage medium and may include any embodiment of a computer program product or other data combination described herein.

Finally, the language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based herein. Accordingly, the disclosure of the embodiments of the invention is intended to be illustrative, but not limiting, of the scope of the invention, which is set forth in the following claims.

What is claimed is:

1. A device comprising:
   (a) an ion sensitive layer;
   (b) an electrically conductive barrier layer as in contact with the ion sensitive layer, wherein the electrically conductive barrier layer is made of a non-metal material;
   (c) a metal layer in direct contact with the electrically conductive barrier layer;
   (d) a metal conductor;
   (e) a polysilicon gate electrically coupled to the metal conductor;
   (f) silicon dioxide ($SiO_2$); and
   (g) a semiconductor substrate,
   wherein the device detects a concentration of at least one target ion in a liquid solution.

2. The device of claim 1, wherein the ion sensitive layer comprises one or more Titanium Oxides.

3. The device of claim 1, wherein the ion sensitive layer is a metal oxide selected from the group consisting of Silicon Nitride, Titanium, Tantalum, Vanadium, Aluminum, Silicon, Yttrium, Tin, one or more alloys of Lead, one or more alloys of Titanium, and combinations thereof.

4. The device of claim 1, wherein the ion sensitive layer is treated by molecular imprinting.

5. The device of claim 4, wherein the molecular imprinting comprises seeding the ion sensitive layer with a plurality of seeding molecules and subsequent partial, entire, substantive, or selective removal of the plurality of seeding molecules from the ion sensitive layer.

6. The device of claim 5, wherein the plurality of seeding molecules are distinct from the at least one target ion in the liquid solution.

7. The device of claim 1, wherein the non-metal electrically conductive barrier layer protects the metal layer from degrading the ion sensitive layer by preventing migration of metal ions from the metal layer to the ion sensitive layer.

8. The device of claim 1, wherein the electrically conductive barrier layer comprises graphene.

9. The device of claim 1, wherein the semiconductor substrate is a P-doped silicon wafer.

10. A device comprising:
(a) at least one ion sensitive layer;
(b) an electrically conductive barrier layer having a top surface and a bottom surface, wherein the electrically conductive barrier layer is made of a non-metal material and the top surface of the electrically conductive barrier layer is connected to the at least one ion sensitive layer;
(c) a metal layer connected to the bottom surface of the electrically conductive barrier layer;
(d) a metal conductor;
(e) a polysilicon gate electrically coupled to the metal conductor;
(f) silicon dioxide ($SiO_2$); and
(g) a semiconductor substrate,
wherein the device detects a concentration of at least one target ion in a liquid solution.

11. The device of claim 10, wherein the at least one ion sensitive layer comprises one or more Titanium Oxides.

12. The device of claim 10, wherein the at least one ion sensitive layer comprises a metal oxide selected from the group consisting of Silicon Nitride, Titanium, Tantalum, Vanadium, Aluminum, Silicon, Yttrium, Tin, one or more alloys of Lead, one or more alloys of Titanium, and combinations thereof.

13. The device of claim 10, wherein the at least one ion sensitive layer is treated by molecular imprinting.

14. The device of claim 13, wherein the molecular imprinting comprises seeding the at least one ion sensitive layer with a plurality of seeding molecules and subsequent partial, entire, substantive, or selective removal of the plurality of seeding molecules from the ion sensitive layer.

15. The device of claim 14, wherein the plurality of seeding molecules are distinct from the at least one target ion in the liquid solution.

16. The device of claim 10, wherein the at least one ion sensitive layer is treated with a polymer film comprising seeding molecules positioned at a top surface of the at least one ion sensitive layer.

17. The device of claim 16, wherein the seeding molecules are selected from the group consisting of calcimycine, beauvericin, carbonyl cyanide m-chlorophenyl hydrazine (CCCP), enniatin, gramicidin A, ionomycin, lasalocid, monensin, nigericin, nonactin, nystatin, salinomycin, valinomycin, cryptands, crown ethers, calixarenes, siderophores, and combinations thereof.

18. The device of claim 10, wherein the device is an ISFET device comprising a first ISFET and a second ISFET, wherein the first ISFET is in proximity to the second ISFET, wherein the at least one ion sensitive layer of the first ISFET is made of the same material as the at least one ion sensitive layer of the second ISFET.

19. The device of claim 18, wherein the at least one ion sensitive layer of the second ISFET is treated to alter ion specificity of the second ISFET from the first ISFET to the at least one target ion.

20. The device of claim 19, wherein the at least one ion sensitive layer of the second ISFET is treated by molecular imprinting.

21. The device of claim 10, wherein the device is a complementary metal-oxide semiconductor (CMOS) ISFET device comprising a first CMOS ISFET and a second CMOS ISFET, wherein the first and/or the second CMOS ISFET is electrically coupled to a reference electrode or a pseudo reference electrode to generate concentration measurements of the at least one target ion in the liquid solution.

22. The device of claim 10, wherein the non-metal electrically conductive barrier layer prevents contamination of the at least one ion sensitive layer by the metal layer by preventing migration of metal ions from the metal layer to the ion sensitive layer.

23. The device of claim 10, wherein the electrically conductive barrier layer comprises graphene.

24. The device of claim 10, wherein the at least one target ion is selected from the group consisting of salts, carboxylic acids, amino acids, hormones, auxins, pesticides, phytohormones, cytokinins, ketones, globins, drugs, sugars, carbohydrates, fertilizers, antigens, enzymes, and aldehydes.

25. The device of claim 10, wherein the device is used as a blood glucose meter, a dialysis machine, a kidney health monitor, a liver health monitor, a heart attack monitor, a breast milk analyzer, a pH meter, an allergen detector, a fat burning monitor, a carbohydrate level detector, a drug testing device, a pregnancy testing device, a cancer detection device, a tap water testing device, a gray water testing device, an aquarium controller, a waste water treatment device, a watershed manager, a swimming pool robot, a soil manager, a plant leaf tester, an agricultural product testing device, a wine analyzer, a chemical sensing device, a livestock or pet health monitor, an oil and gas waste treatment and recovery device, or a human performance testing device.

26. The device of claim 10, wherein the device is an ISFET or a complementary metal-oxide semiconductor (CMOS) ISFET.

27. A device comprising:
(a) an ion sensitive layer;
(b) a passivation layer, wherein the passivation layer is capable of being ground, polished, etched, or planarized;
(c) an electrically conductive barrier layer connected to the ion sensitive layer, wherein the electrically conductive barrier layer is made of a non-metal material;
(d) a top metal layer connected to the electrically conductive barrier layer;
(e) a metal conductor;
(f) a polysilicon gate electrically coupled to the metal conductor;
(g) silicon dioxide ($SiO_2$); and
(h) a semiconductor substrate,
wherein the device detects a concentration of at least one target ion in a liquid solution.

28. The device of claim 27, wherein the ion sensitive layer comprises one or more Titanium Oxides.

29. The device of claim 27, wherein the ion sensitive layer is a metal oxide selected from the group consisting of Silicon Nitride, Titanium, Tantalum, Vanadium, Aluminum, Silicon, Yttrium, Tin, one or more alloys of Lead, one or more alloys of Titanium, and combinations thereof.

30. The device of claim 27, wherein the ion sensitive layer is treated by molecular imprinting.

31. The device of claim 30, wherein the molecular imprinting comprises seeding the ion sensitive layer with a plurality of seeding molecules and subsequent partial, entire, substantive, or selective removal of the plurality of seeding molecules from the ion sensitive layer.

32. The device of claim 31, wherein the plurality of seeding molecules are distinct from the at least one target ion in the liquid solution.

33. The device of claim 27, wherein the non-metal electrically conductive barrier layer protects the metal layer from degrading the ion sensitive layer by preventing migration of metal ions from the metal layer to the ion sensitive layer.

34. The device of claim 27, wherein the electrically conductive barrier layer comprises graphene.

35. The device of claim 27, wherein the semiconductor substrate is a P-doped silicon wafer.

* * * * *